(12) United States Patent
Derwin et al.

(10) Patent No.: US 11,013,590 B2
(45) Date of Patent: *May 25, 2021

(54) REINFORCED TISSUE GRAFT

(71) Applicant: THE CLEVELAND CLINIC FOUNDATION, Cleveland, OH (US)

(72) Inventors: Kathleen A. Derwin, Shaker Heights, OH (US); Joseph P. Iannotti, Strongsville, OH (US); Sambit Sahoo, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/701,763

(22) Filed: May 1, 2015

(65) Prior Publication Data
US 2015/0230913 A1    Aug. 20, 2015

Related U.S. Application Data

(63) Continuation of application No. 13/727,650, filed on Dec. 27, 2012, now abandoned, which is a
(Continued)

(51) Int. Cl.
*A61L 27/36* (2006.01)
*A61F 2/02* (2006.01)
(Continued)

(52) U.S. Cl.
CPC .............. *A61F 2/02* (2013.01); *A61F 2/08* (2013.01); *A61L 27/34* (2013.01);
(Continued)

(58) Field of Classification Search
CPC ............. A61L 27/3633; A61L 27/3604; A61F 2/0063; A61F 2/02; A61F 2210/0076
See application file for complete search history.

(56) References Cited

U.S. PATENT DOCUMENTS 6,551,356 B2    4/2003   Rousseau
6,638,312 B2   10/2003   Plouhar et al.
(Continued)

FOREIGN PATENT DOCUMENTS

EP        1177800 A1     6/2002
WO     03007847 A1     1/2003
(Continued)

OTHER PUBLICATIONS

Singapore Search Report and Written Opinion for Application No. 11201503367V, dated Mar. 18, 2016, pp. 1-7.
(Continued)

*Primary Examiner* — Shaun L David
*Assistant Examiner* — Christina C Lauer
(74) *Attorney, Agent, or Firm* — Tarolli, Sundheim, Covell & Tummino LLP

(57) ABSTRACT

A biocompatible tissue graft includes a first layer of a bioremodelable collageneous material, a second layer of biocompatible synthetic or natural remodelable or substantially remodelable material attached to the first layer; and at least one fiber that is stitched in a reinforcing pattern in the first layer and/or second layer to mitigate tearing and/or improve fixation retention of the graft, and substantially maintain the improved properties while one or more of the layers is remodeling.

10 Claims, 13 Drawing Sheets

Related U.S. Application Data continuation-in-part of application No. 12/934,791, filed as application No. PCT/US2009/038570 on Mar. 27, 2009, now abandoned, application No. 14/701,763, which is a continuation-in-part of application No. PCT/US2011/042138, filed on Jun. 28, 2011.

(60) Provisional application No. 61/359,067, filed on Jun. 28, 2010, provisional application No. 61/040,066, filed on Mar. 27, 2008.

(51) Int. Cl.

| | |
|---|---|
| A61F 2/08 | (2006.01) |
| A61L 27/38 | (2006.01) |
| A61L 27/48 | (2006.01) |
| A61L 27/34 | (2006.01) |

(52) U.S. Cl.
CPC ........... *A61L 27/3633* (2013.01); *A61L 27/38* (2013.01); *A61L 27/48* (2013.01); *A61F 2210/0076* (2013.01); *A61L 2420/04* (2013.01); *A61L 2420/08* (2013.01)

(56) References Cited

U.S. PATENT DOCUMENTS

| | | | |
|---|---|---|---|
| 6,736,854 | B2 | 5/2004 | Vadurro et al. |
| 6,800,082 | B2 | 10/2004 | Rousseau |
| 6,902,932 | B2 | 6/2005 | Altman et al. |
| 7,160,333 | B2 | 1/2007 | Plouhar et al. |
| 7,569,233 | B2 | 8/2009 | Malaviya et al. |
| 7,615,065 | B2 | 11/2009 | Priewe et al. |
| 2001/0002446 | A1 | 5/2001 | Plouhar et al. |
| 2002/0103542 | A1 | 8/2002 | Bilbo |
| 2003/0143207 | A1 | 7/2003 | Livesey et al. |
| 2004/0006395 | A1 | 1/2004 | Badylak |
| 2004/0078090 | A1 | 4/2004 | Binette et al. |
| 2005/0249771 | A1 | 11/2005 | Malaviya et al. |
| 2005/0249772 | A1 | 11/2005 | Malaviya et al. |
| 2006/0253203 | A1 | 11/2006 | Alvarado |
| 2006/0282173 | A1 | 12/2006 | McFetridge |
| 2006/0286144 | A1 | 12/2006 | Yang et al. |
| 2007/0162103 | A1 | 4/2007 | Case et al. |
| 2007/0129811 | A1 | 6/2007 | Plouhar et al. |
| 2007/0190108 | A1 | 8/2007 | Datta et al. |
| 2007/0224238 | A1 | 9/2007 | Mansmann et al. |
| 2007/0276507 | A1 | 11/2007 | Bertram et al. |
| 2008/0027542 | A1 | 1/2008 | McQuillan et al. |
| 2008/0038352 | A1 | 2/2008 | Simpson et al. |
| 2008/0044900 | A1 | 2/2008 | Mooney et al. |
| 2008/0188936 | A1 | 8/2008 | Ball et al. |
| 2008/0281421 | A1 | 11/2008 | Cahn et al. |
| 2009/0018655 | A1 | 1/2009 | Brunelle et al. |
| 2009/0306688 | A1 | 12/2009 | Patel et al. |
| 2009/0318752 | A1 | 12/2009 | Evans et al. |
| 2010/0020477 | A1 | 1/2010 | Chen et al. |
| 2010/0028396 | A1 | 2/2010 | Ward et al. |
| 2010/0063599 | A1 | 3/2010 | Brunelle et al. |
| 2010/0185219 | A1 | 7/2010 | Gertzman et al. |

FOREIGN PATENT DOCUMENTS

| | | |
|---|---|---|
| WO | 2007047743 A2 | 4/2007 |
| WO | 2009120966 A2 | 10/2009 |
| WO | 2010059783 A2 | 5/2010 |
| WO | 2012047338 A2 | 4/2012 |

OTHER PUBLICATIONS

Singapore Search Report and Written Opinion for Application No. 11201503364U, dated May 9, 2016, pp. 1-7.

Cheng et al. "Targeted Migration of Mesenchymal Stem Cells Modified with CXCR4 Gene to Infarcted Myocardium Improves Cardiac Performance", Molecular Therapy, 16:571-579 (2006).

Post, "Pectoralis Major Transfer for Winging of the Scapula", J. Shoulder Elbow Surg., 4:1-9 (1995).

McCarron et al., "Reinforced Fascia Patch Limits Cyclic Gapping of Rotator Cuff Repairs in a Human Cadaveric Model", Journal of Shoulder and Elbow Surgery, 2012, pp. 1-7.

Itani et al., "Prospective Study of Single-Stage Repair of Contaminated Hernias using a Biologic Porcine Tissue Matrix: The RICH Study", Surgery, 2012, vol. 152, No. 3, pp. 498-505.

Haas et al., "Reconstruction of Combined Defects of the Achilles Tendon and the Overlying Soft Tissue With a Fascia Lata Graft and a Free Fasciocutaneous Lateral Arm Flap", Annals of Plastic Surgery, 2003, vol. 51, pp. 376-382.

Bright et al., "Freeze-Dried Fascia Lata Allografts: A Review of 47 Cases", Journal of Pediatric Orthopedics, 1981, vol. 1, No. 1, pp. 13-22.

Baker et al., "Does Augmentation with a Reinforced Fascia Patch Improve Rotator Cuff Repair Outcomes?", Clinical Orthopaedics and Related Research, 2012, vol. 470, No. 9, pp. 2513-2521.

Aurora et al., "Mechanical Characterization and Biocompatibility of a Novel Reinforced Fascia Patch for Rotator Cuff Repair", Journal of Biomedical Materials Research A, 2011, vol. 99A, Issue 2, pp. 221-230.

International Search Report and Written Opinion, dated Mar. 13, 2014, pp. 1-8.

International Search Report and Written Opinion, dated Mar. 6, 2014, pp. 1-12.

International Search Report and Written Opinion, dated Mar. 6, 2014, pp. 1-11.

Shiyamaladevi et al., "Characterization of Seam Strength and Seam Slippage on Cotton Fabric with Woven Structures and Finish", Res. J. Engineering Sci, vol. 1(2), 41-50, Aug. 2012.

Tong et al., "Chapter 8 Stitched Composites", 3D Fibre Reinforced Polymer Composites, Elsevier Science Ltd., 2002, pp. 162-204.

Sauri et al., "A Factorial Study of Seam Resistance: Woven and Knitted Fabrics", Indian Journal of Textile Research, vol. 12, Dec. 1987, pp. 188-193.

Murugesan et al., "Characterization of Sewability Parameters of Plain Structured Fabric with Structurally Modified Trevira CS Yarn for Defence Application", Chemical Science Review and Letters, 2012, 1(2), pp. 53-61.

Mouritz et al., "A Review of the Effect if Stitching on the In-Plane Mechanical Properties of Fibre-Reinforced Polymer Composites", Composites Part A 28A, (1997), pp. 979-991.

Leikina et al., "Type I Collagen is Thermally Unstable at Body Temperature", PNAS, Feb. 5, 2002, vol. 99, No. 3, pp. 1314-1318.

Gurarda et al., "The Effects of Elastane Yarn Type and Fabric Density on Sewing Needle Penetration Forces and Seam Damage of PET-Elastane Woven Fabrics", Fibres & Textiles in Eastern Europe, Oct./Dec. 2007, vol. 15, No. 4 (63), pp. 73-76.

Gribaa et al., "Influence of Sewing Parameters Upon the Tensile Behavior of Textile Assembly", International Journal of Clothing Science and Technology, vol. 18, No. 4, 2006, pp. 235-247.

Dransfield et al., "Improving the Delamination Resistance of CFRP by Stitching—A Review", Composites Science and Technology, 50 (1994), pp. 305-317.

Danielsen, "Age-Related Thermal Stability and Susceptibility to Proteolysis of Rat Bone Collagen", Biochem J. (1990), 272, pp. 697-701.

Choudhary et al., "Research Article Effect of Some Fabric and Sewing Conditions on Apparel Seam Characteristics", Journal of Textiles, vol. 2013, pp. 1-7.

Cheng et al., "Studies on the Seam Properties of Some Selected Woven Fabrics", Institute of Textiles and Clothing, The Hong Kong Polytechnic University, Hung Hom, Kowloon, Hong Kong, pp. 486-496.

Aurora et al., "Commercially Available Extracellular Matrix Materials for Rotator Cuff Repairs: State of the Art and Future Trends", J Shoulder Elbow Surg, Sep./Oct. 2007, pp. 171S-178S.

(56) References Cited

OTHER PUBLICATIONS

Designation D 1908-81, "Standard Test Method for Needle-Related Damage Due to Sewing in Woven Fabric", ASTM International, pp. 384-388.
Anon, "The Stitching of Fabrics, Part IV. The Strength of Seams", Shirley Institute Bulletin, 1939, pp. 164-175.
Communication pursuant to Article 94(3) EPC, for Application No. 09 724 439.6, dated Oct. 2, 2015, pp. 1-4.
Karahan et al., "Influence of Stitching Parameters on Tensile Strength of Aramid/Vinyl Ester Composites." Materials Science 19.1 (2013): 67-72.
Namiranian, et al. "Seam slippage and seam strength behavior of elastic woven fabrics under static loading." Indian Journal of Fibre & Textile Research (IJFTR) 39.3 (2014): 221-229.
"Standard Test Method for Bursting Strength of Textiles—Constant-Rate-of-Traverse (CRT) Ball Burst Test", ASTM International, Designation: D 3787-01, pp. 1-4.
Korean office action for corresponding International Patent Application PCT/US2013/067524 dated Aug. 2, 2016.
Korean office action for corresponding International Patent Application PCT/US2013/067514 dated Sep. 30, 2016.
Singapore office action for corresponding International Patent Application 11201503367V dated Oct. 11, 2016.
Singapore office action for corresponding International Patent Application 11201503364U dated May 17, 2016.

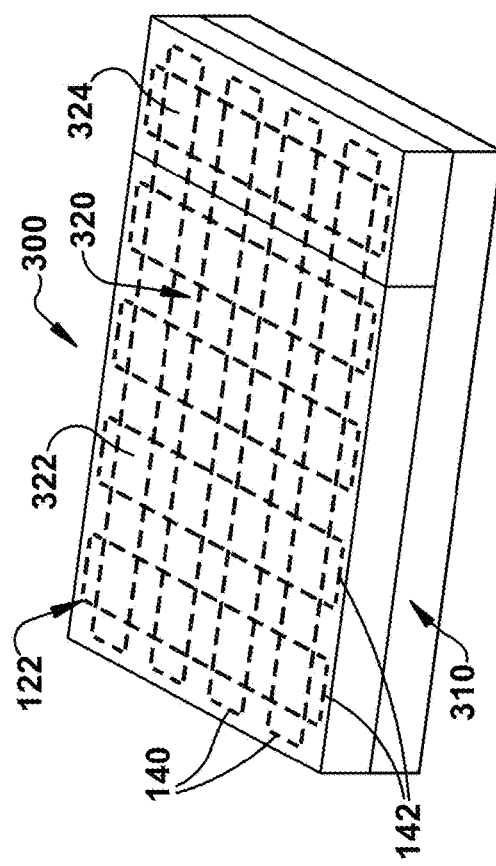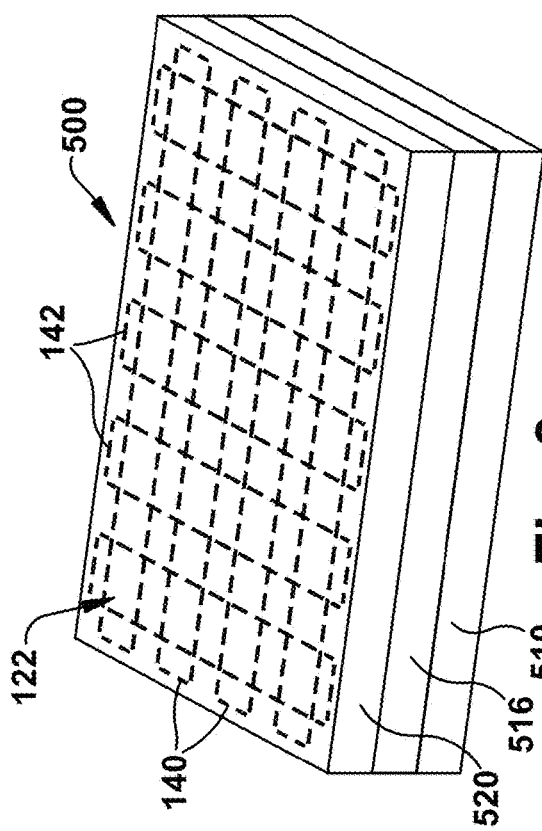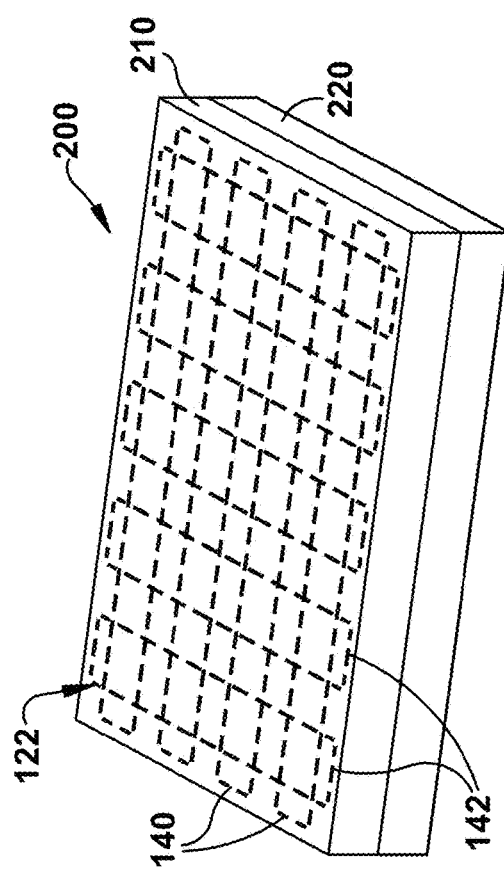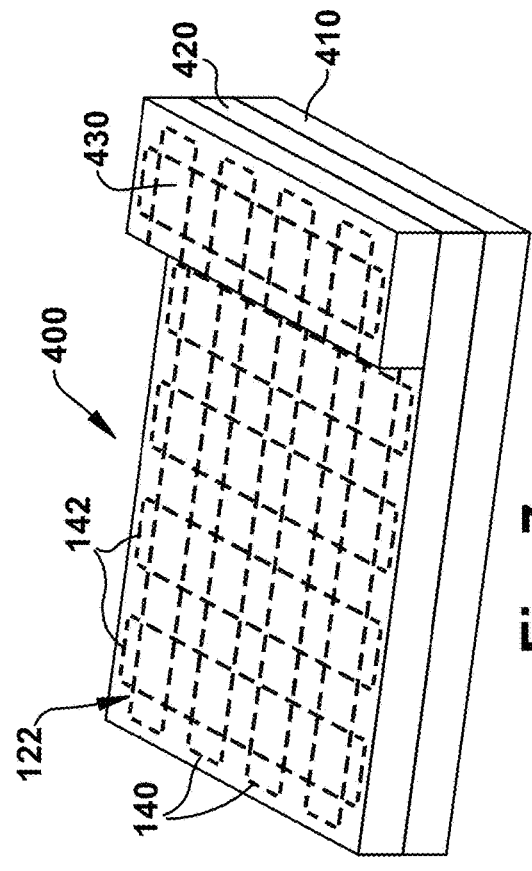

Fig. 21. Cumulative cyclic elongation (CCE) curves of native and fiber-reinforced dermis patches before and after enzymatic degradation.

REINFORCED TISSUE GRAFT

RELATED APPLICATIONS

This application is a Continuation of U.S. patent application Ser. No. 13/727,650, filed Dec. 27, 2012, which is a Continuation-in-part of U.S. patent application Ser. No. 12/934,791, filed Sep. 27, 2010, which is a National phase filing of PCT/US2009/038570, filed Mar. 27, 2009, which claims priority from U.S. Provisional Application Ser. No. 61/040,066, filed Mar. 27, 2008, and also claims priority from U.S. Provisional Application Ser. No. 61/720,173, filed Oct. 30, 2012. This application is also a Continuation-in-Part of International Application No. PCT/US2011/042138, filed Jun. 28, 2011, which claims priority from U.S. Provisional Application No. 61/359,067, filed Jun. 28, 2010. The subject matter of each of the aforementioned applications is incorporated herein by reference in its entirety.

TECHNICAL FIELD

The present invention is directed to tissue grafts and, in particular, is directed to a multilayered, reinforced tissue graft.

BACKGROUND OF THE INVENTION

Researchers have experienced major challenges in designing methods to repair abdominal wall defects that result from traumatic injuries, surgical procedures (incisional hernias) or chronic diseases. Currently available synthetic and biological grafts have demonstrated only limited success. The graft should be biocompatible, have adequate mechanical properties and should also degrade at an appropriate rate to permit transition of function from the graft to native fascia. While the use of synthetic meshes has lowered incidence rates of incisional hernias to below 10%, these repairs are still frequently complicated by infection, visceral adhesion, extrusion and fistulation, and require re-operation. Biological grafts derived from decellularized tissues, such as dermis or small intestinal submucosa (SIS), have shown greater success than synthetics. They are better vascularized, less prone to be complicated by visceral adhesions, and can be used in the presence of contaminated or infected fields. While grafts derived from acellular dermis possess biomechanical properties that are similar to abdominal wall fascia, and have shown promise for hernia repair, they lose mechanical strength and integrity after implantation, resulting in laxity, stretching and poor suture retention, which in turn can lead to complications, such as bulging, dehiscence, and hernia recurrence. The dermis products are also commonly available in small sizes, and require pre-operative suturing of multiple pieces to repair large hernia defects.

SUMMARY

This application relates to a biocompatible tissue graft that includes a first layer of a bioremodelable collagenous material and a second layer of biocompatible synthetic or natural remodelable, substantially remodelable, or non-remodelable material attached to the first layer. The graft further includes at least one fiber that is stitched in a reinforcing pattern in the first layer and/or second layer to mitigate tearing and/or improve fixation retention of the graft, and substantially maintain the improved properties while one or more layers of the graft remodels.

The first layer can include an extracellular matrix, and the second layer can include an extracellular matrix, a biocompatible substantially remodelable synthetic material, or a biocompatible non-remodelable synthetic material.

The fiber can include a natural or synthetic material and be stitched into at least one of the first layer and/or the second layer in, for example, a cross-hatched configuration or a concentric pattern. In one example, the first layer and the second layer can be stitched together with the fiber. In some embodiments, the fiber can be selected from the group consisting of collagen, silk, sericin free silk, modified silk fibroins, polyesters like PGA, PLA, polylactic-co-glycolic acid (PLGA), polyethyleneglycol (PEG), polyhydroxyalkanoates (PHA), polyethylene terephthalate (PET), polyethylene (PE), ultra-high molecular weight polyethylene (UHMWPE), blends thereof, and copolymers thereof.

In an aspect of the application, the first layer and/or the second layer can include extracellular matrix that is decellularized. The first layer and/or the second layer can also be seeded with at least one differentiated cell or progenitor cell. The first layer and/or the second layer can further include at least one biologically active molecule selected from the group consisting of drugs, sclerosing agents, enzymes, hormones, cytokines, colony-stimulating factors, vaccine antigens, antibodies, clotting factors, angiogenesis factors, regulatory proteins, transcription factors, receptors, structural proteins, nucleic acid therapeutic agents, such as plasmids, vectors, siRNA, and micro-RNA, and combinations thereof.

This application also relates to a method of constructing a biocompatible tissue graft. The method includes providing an extracellular matrix layer, providing a synthetic layer, attaching the extracellular matrix layer to the synthetic layer, and stitching at least one fiber into the layers in a reinforcement pattern to mitigate tearing and/or improve fixation retention of the graft, and substantially maintain the improved properties while one or more layers of the graft remodels.

The method can further include providing a second extracellular matrix layer and attaching the second extracellular layer to the first extracellular layer and/or the synthetic layer. The fiber can be stitched into the extracellular matrix layers and the synthetic layer in a reinforcement pattern to mitigate tearing and/or improve fixation retention of the graft, and substantially maintain the improved properties while one or more layers of the graft remodels.

In an aspect of the application, the second extracellular matrix layer is provided only at one end of the tissue graft.

The fiber can include a natural or synthetic material and be stitched into at least one of the first extracellular matrix layer, the second extracellular matrix layer, and/or the synthetic layer in, for example, a cross-hatched configuration or a concentric pattern. The first extracellular matrix layer, the second extracellular layer, and/or the synthetic layer can also be stitched together with the fiber.

In another aspect of the application, the graft can have a multilayer construction and include a first layer, a second layer, and a third layer. The first layer, the second layer, or the third layer can comprise at least one layer of an extracellular matrix and at least one layer of a biocompatible substantially remodelable synthetic material or biocompatible non-remodelable synthetic material. The first layer, the second layer, and/or third layer can be stitched together with a fiber. In one example, the first layer and the second layer can be stitched together with the fiber. In another example, the first layer, the second layer, and the third layer can be stitched together with the fiber. The fiber can be stitched into the extracellular matrix layer(s) and optionally the synthetic layer(s) in a reinforcement pattern to mitigate tearing and/or improve fixation retention of the graft, and substantially maintain the improved properties while one or more layers of the graft remodels.

In some embodiments, the fiber can be selected from the group consisting of collagen, silk, sericin free silk, modified silk fibroins, polyesters like PGA, PLA, polylactic-co-glycolic acid (PLGA), polyethyleneglycol (PEG), polyhydroxyalkanoates (PHA), polyethylene terephthalate (PET), polyethylene (PE), ultra-high molecular weight polyethylene (UHMWPE), blends thereof, and copolymers thereof.

An aspect of the application also relates to a biocompatible tissue graft that includes a first layer of a bioremodelable collageneous material. A second layer of biocompatible synthetic or natural remodelable or substantially remodelable material is attached to the first layer. At least one fiber is stitched in a reinforcing pattern in the first layer and/or second layer to mitigate tearing of the graft, improve the fixation retention of the graft, and/or limit cyclic stretching of the graft and substantially maintain these properties following partial enzymatic degradation of the graft while one or more of its layers remodels. The at least one fiber has at least one free end that extends beyond a peripheral surface of the tissue graft for securing the tissue graft to a host tissue.

The fiber can be formed from a biocompatible material and have a high modulus of elasticity and failure load. Examples of biocompatible materials that can be used to form the fiber include silk, sericin-free silk, modified silk fibroin, polyesters, such as poly(glycolic acid) (PGA), poly(lactic acid) (PLA), poly(ethylene glycol) (PEG), polyhydroxyalkanoates (PHA) and polyethylene terephthalate (PET), medical grade polyethylene, such as polyethylene (UHMWPE), blends thereof and copolymers thereof, as well as other biocompatible materials that are typically used in forming biocompatible fibers for in vivo medical applications. The fiber can additionally be radio-opaque (e.g., by adding an opacifier, such as barium sulfate or tantalum to the fiber).

Another aspect of the application relates to a method of constructing a biocompatible tissue graft. The method includes providing a tissue graft that includes a first layer of a bioremodelable collageneous material and a second layer of biocompatible synthetic or natural remodelable or substantially remodelable material. At least one fiber is stitched into at least one of the layers in a reinforcement pattern to mitigate tearing of the graft, improve the fixation retention of the graft, and/or limit cyclic stretching of the graft and substantially maintain these properties following partial enzymatic degradation of the graft while one or more of its layers remodels. The at least one fiber can have a free end that extends beyond a peripheral surface of the graft and is effective for securing the graft to a host tissue.

A further aspect of the application relates to a method for repairing tissue in a subject. The method includes providing a tissue graft that includes a first layer of a bioremodelable collageneous material, a second layer of biocompatible synthetic or natural remodelable or substantially remodelable material attached to the first layer, and at least one fiber stitched in a reinforcing pattern in the first layer and/or second to mitigate tearing of the graft, improve the fixation retention of the graft, and/or limit cyclic stretching of the graft and substantially maintain these properties following partial enzymatic degradation of the graft while one or more of its layers remodels. The at least one fiber having at least one free end extending beyond a peripheral surface of the tissue graft for securing the tissue graft to a host tissue. A free end of the at least one fiber that extends beyond the peripheral surface of the graft is secured to the tissue in the subject.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIGS. 5-8 are schematic illustrations of multilayer tissue grafts in accordance with yet another embodiment of the present invention;

DETAILED DESCRIPTION

Figure 1:
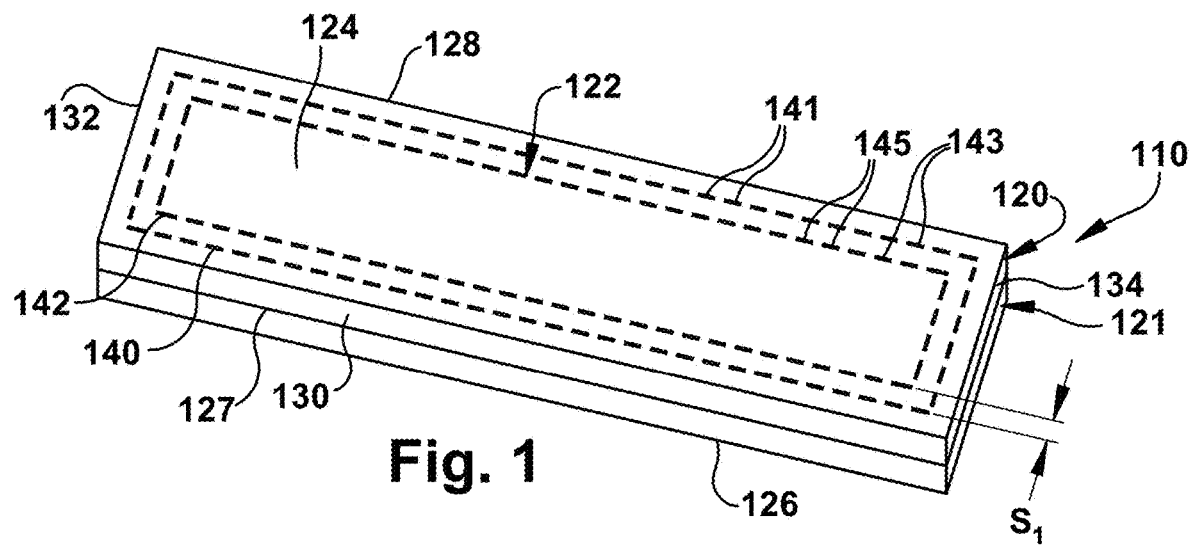
FIG. 1 is schematic illustration of a multilayer tissue graft having reinforcement means in accordance with an embodiment of the present invention.

The present invention is directed to biocompatible tissue grafts and, in particular, is directed to a multilayered, fiber-reinforced tissue graft with improved fixation retention, suture retention, and biomechanical strength properties. The fiber includes at least one free end that extends beyond the periphery of the tissue graft for securing the graft to host tissue. The tissue graft can be used to treat a tissue defect of a subject (e.g., human being), such as a musculoskeletal defect, or in tendon-to-bone repairs (e.g., rotator cuff injury), or soft-tissue repairs, such as the repair of lacerated muscles, muscle transfers, or use in tendon reinforcement. The tissue graft may also be used as a bridging material in a subject in the case where the gap between a tendon and the associated bone is too large to repair conventionally. The tissue graft can be incorporated between the bone-tendon interface and fixed to the bone and tendon to repair a gap or tear.

The term "biocompatible" as used herein refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1. Typically, these tests measure a material's toxicity, infectivity, pyrogenicity, irritation potential, reactivity, hemolytic activity, carcinogenicity and/or immunogenicity. A biocompatible material, when introduced into a majority of patients, will not cause an undesirably adverse, long-lived or escalating biological reaction or response, and is distinguished from a mild, transient inflammation, which typically accompanies surgery or implantation of foreign objects into a living organism.

The biocompatible tissue graft can be used as an overlay (i.e., over or at the interface of the repair), an interpositional (i.e., to fill a space between a tissue and its attachment), or an underlay (i.e., under or at the interface of the repair). In one example, the tissue graft can be applied over the bone-tendon repair site and fixed to the bone and tendon to augment the repair. In another example, the tissue graft can be used to repair an abdominal wall injury site or abdominal wall hernia. Abdominal hernias can be repaired by onlay, inlay, or underlay techniques, where the graft is placed over, within, or under the defect in the abdominal wall muscle. The underlay technique involves placing the tissue graft beneath the abdominal musculature (underlying the hernia defect and extending beyond it), and anchoring the edges of the graft to the muscle using sutures.

In accordance with an aspect of the application, the biocompatible tissue graft can include a first layer of bioremodelable collagenous material and a second layer of biocompatible resorbable or non-resorbable synthetic or natural remodelable, substantially remodelable, or non-remodelable material attached to the first layer. The first and second layers define a peripheral surface of the tissue graft. At least one fiber is stitched in a reinforcing pattern in the first layer, second layer, or both the first layer and second layer to mitigate tearing of the graft, improve the fixation retention of the graft, and/or limit cyclic stretching of the graft and substantially maintain these properties following partial enzymatic degradation of the graft while one or more of its layers remodels. The at least one fiber includes at least one free end that extends beyond the peripheral surface for securing the tissue graft to a host tissue.

The terms "remodelable" and "bioremodelable" as used herein refer to the ability of the material to be resorbed by the host and replaced by host tissue (i.e., remodeled from one material to another). Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization are typically observed over a period of about 5 days to about 6 months or longer, as the remodelable material acts as a matrix for the ingrowth of adjacent tissue with site-specific structural and functional properties. The remodelable material may be completely or partially resorbed and replaced by the host during this time period.

The term, "substantially remodelable" materials as used herein include materials that are unlikely to be completely resorbed and replaced by host tissue. These materials can permit tissue ingrowth at a much slower rate than the rate of tissue growth in the remodelable material. Tissue growth through the substantially remodelable material is typically only observable after sufficient periods of implantation in a body vessel that permit substantial amounts of tissue growth in the remodelable material.

By substantially maintaining "the improved properties while one or more layers of the graft remodels", it is meant that the improved fixation properties, such as suture retention properties, are maintained or minimally decreased after implantation of the graft in vivo due to, for example, collagenase digestion of the remodelable or substantially remodelable layers, while the remodelable or substantially remodelable layers of the graft are resorbed by the host and replaced by host tissue and until the host tissues have sufficient strength.

In some instances, the bioremodelable collagenous material used to form the first layer can include at least one sheet of the mammalian-derived ECM. The ECM can be derived from any mammalian ECM, such as fascia, and in particular, fascia lata from humans. The ECM can be derived from other connective tissue materials, such as dermis as long as the ECM is biocompatible with the target site or the tissue injury being treated in the subject or both. The ECM can also be derived, for example, from other tissues and/or other materials, such as collagen, skin, bone, articular cartilage, meniscus, myocardium, periosteum, artery, vein, stomach, large intestine, small intestine (such as SIS), peritoneum, mesothelium, diaphragm, tendon, ligament, neural tissue, meninges, striated muscle, smooth muscle, bladder, ureter, abdominal wall fascia, and combinations thereof.

The ECM used to form the first layer may be obtained directly from mammalian tissue (such as an autograft, allograft or xenograft). These tissues may be obtained from patients at the time of surgery or a commercial source, such as a tissue bank medical device company. ECM obtained from tissue banks and other commercial sources may be formed using proprietary processing techniques or modified by additional processing techniques before it is used. In one example, these techniques can be used to remove cells and other potentially infectious agents from the ECM.

In other instances, the bioremodelable collagenous material used to form the first layer can comprise a collagenous sheet that is derived from a mammalian source or is plant-based. For example, the collagenous sheet may constitute collagen that is derived from the peritoneum of pigs (Kensey Nash ECM Surgical Patch manufactured by Kensey Nash Corporation of Exton, Pa.). In another example, the collagenous sheet may constitute collagen that is derived from the Procollagen of plants and sold under the trade name COLLAGE RH (manufactured by CollPlant of Ness-Ziona, Israel). The COLLAGE RH may be formed by collecting Procollagen from plants and processing it into pure, fibrin forming collagen.

In some instances, the second layer can be formed from a bioremodelable collagenous material as described above, a substantially remodelable synthetic or natural material, or a non-remodelable synthetic material. In an aspect of the application, the second layer, when attached to the first layer, can structurally reinforce and/or mechanically enhance the first layer and the tissue graft. For example, the second layer can exhibit a construction that facilitates retention of the reinforcing means in the tissue graft and thereby helps to enhance and/or substantially maintain suture retention as the first layer remodels and prevents relative movement between the first layer and the second layer.

In some examples described herein, the second layer can include a two-dimensional or three-dimensional fibrous matrix or mesh construct, which may be shaped or formed for the particular application. Typically, the mesh is a pliable material, such that it has sufficient flexibility to be wrapped around the external surface of a body passageway or cavity, or a portion thereof. The mesh may be capable of providing support to the graft. In certain aspects, the mesh may be adapted to release an amount of a therapeutic agent.

Mesh materials may take a variety of forms. For example, the mesh may be in a woven, knit, or non-woven form and may include fibers or filaments that are randomly oriented relative to each other or that are arranged in an ordered array or pattern. In one aspect, the mesh may be in the form of a fabric, such as a knitted, braided, crocheted, woven, non-woven (e.g., a melt-blown, wet-laid, or electrospun) or webbed fabric. In one aspect, the mesh may include a natural or synthetic biodegradable polymer that may be formed into a knit mesh, a weave mesh, a sprayed mesh, a web mesh, a braided mesh, a looped mesh, and the like. Preferably, the mesh has intertwined threads that form a porous structure, which may be, for example, knitted, woven, or webbed.

The structure and properties of the mesh used in the graft can depend on the application and the desired mechanical (i.e., flexibility, tensile strength, and elasticity) and degradation properties, and the desired loading and release characteristics for selected therapeutic agent(s). The mesh should have mechanical properties such that the graft can remain sufficiently strong until the surrounding tissue has healed. Factors that affect the flexibility and mechanical strength of the mesh include, for example, the porosity, fabric thickness, fiber diameter, polymer composition (e.g., type of monomers and initiators), process conditions, and the additives that are used to prepare the material.

Typically, the mesh possesses sufficient porosity to permit the flow of fluids through the pores of the fiber network and to facilitate tissue ingrowth. Generally, the interstices of the mesh should be wide enough apart to allow light visible by eye, or fluids, to pass through the pores. However, materials having a more compact structure also may be used. The flow of fluid through the interstices of the mesh may depend on a variety of factors, including, for example, the stitch count or thread density. The porosity of the mesh may be further tailored by, for example, filling the interstices of the mesh with another material (e.g., particles or polymer) or by processing the mesh (e.g., by heating) in order to reduce the pore size and to create non-fibrous areas. Fluid flow through the mesh can vary depending on the properties of the fluid, such as viscosity, hydrophilicity/hydrophobicity, ionic concentration, temperature, elasticity, pseudoplasticity, particulate content, and the like. In one example, the interstices of the mesh can be large enough so as to not prevent the release of impregnated or coated therapeutic agent(s) from the mesh, and the interstices preferably do not prevent the exchange of tissue fluid at the application site.

Mesh materials can also be sufficiently flexible so as to be capable of conforming to the shape of an anatomical surface and/or the first layer. In certain cases, the mesh material may be sufficiently flexible so as to be capable of being wrapped around all or a portion of the first layer and/or the external surface of a body passageway or cavity. Flexible mesh materials are typically in the form of flexible woven or knitted sheets having a thickness ranging from about 25 microns to about 3000 microns; preferably from about 50 to about 1000 microns. Mesh materials for use in the practice of the invention typically range from about 100 to 400 microns in thickness.

In some instances, the second layer may be formed of any one or combination of known biocompatible, synthetic or natural materials, including polypropylene (PP), polyurethane (PU), expanded polytetrafluoroethylene (ePTFE), polylactic acid (PLA), polyglycolic acid (PGA), polycaprolactone (PCL), polydioxanone (PDO), trimethylene carbonate (TMC), polyvinyl alcohol (PVA), poly(ethylene oxide), poly(acrylic acid), poly(vinyl alcohol), poly(N-isopropyl acrylamide), poly(vinyl pyrrolidone) (PVP), poly (methacrylic acid), poly(p-styrene carboxylic acid), poly(p-styrenesulfonic acid), poly(vinylsulfonicacid), poly(ethyleneimine), poly(vinylamine), poly(anhydride), poly(HEMA), polyhydroxybutyrate (PHB), silk, ECM materials, such as decellularized SIS, UBM, muscle, fibronectin, fibrin, fibrinogen, collagen, fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin), proteins found in basement membranes, and fibrosin), albumin, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids). These compositions include copolymers of the above polymers as well as blends and combinations of the above polymers.

In one example, the second layer is constructed of a medical-grade polypropylene mesh fabric commercially available from ATEX technologies, Inc. (Pinebluff, N.C.). In another example, the second layer is constructed of a polylactic acid mesh (X-Repair) available from Synthasome, Inc. (San Diego, Calif.).

The reinforcing means can include any structure or material that is applied to the first layer and/or second layer, is capable of mitigating tearing of the graft when the graft is fixed to tissue being treated, is capable of increasing or improving the fixation retention properties of the tissue graft beyond that which is present in a first and second layers alone, and/or can limit the cyclic stretching of the graft, and substantially maintain these properties following partial enzymatic degradation of the graft while one or more of its layers remodels. The fixation retention properties can be tailored to increase the graft's ability to remain secured to anatomic structures, such as bone and soft tissues, when used to treat a tissue defect. The multilayer graft may be secured to these anatomical structures by, for example, weaving, screws, staples, sutures, pins, rods, other mechanical or chemical fastening means or combinations thereof. For instance, the graft may be secured to the treated tissue via different suture configurations, such as, massive cuff, mattress stitching and simple suture and different fixation techniques, such as, Synthes screw or Biotenodesis screw fixation and suture anchors with a Krakow stitch.

In one aspect of the invention, the reinforcing means can include a thread or strands of fiber(s) that are stitched in a reinforcement pattern in the tissue graft. Fiber stitched in a reinforcement pattern can increase the fixation properties of the tissue graft, which will result in a tissue graft having improved mechanical properties for implantation and repair of anatomical defects in a subject. The reinforcement pattern can include any stitch pattern that mitigates tearing of the graft, improves the fixation retention of the graft, and/or limits cyclic stretching of the graft and substantially maintain these properties following partial enzymatic degradation of the graft while one or more of its layers remodels. For example, the stitch pattern can include one or more generally concentric, peripheral or cross-hatched stitch patterns.

The fiber can enhance the fixation retention, mitigate tearing, and limit cyclic stretching of the tissue graft once stitched into the graft. The fiber can be formed from a biocompatible material that is bioresorbable, biodegradable, or non-resorbable. The term bioresorbable is used herein to mean that the material degrades into components, which may be resorbed by the body and which may be further biodegradable. Biodegradable materials are capable of being degraded by active biological processes, such as enzymatic cleavage.

One example of a biocompatible material that can be used to form the fiber is silk. The silk may include, for example, sericin-free silk fibroin or silk-fibroin modified with a peptide sequence that sequesters growth factors in vivo, such as disclosed in U.S. Pat. No. 6,902,932, which is herein incorporated by reference. The fibers can also be formed from biodegradable polymers including poly(glycolic acid) (PGA), poly(lactic acid) (PLA), poly(lactic-co-glycolic acid) (PLGA), poly(ethylene glycol) (PEG), blends thereof, and copolymers thereof. By way of example, the reinforcing fiber may include a core of PGA surrounded by a sheath of reinforced PLA fibers. The PGA and PLA may be obtained, for example, from Concordia Fibers in Coventry, R.I. Other examples of biocompatible polymers that can be used to form the fiber are resorbable polyesters, such as polyhydroxyalkanoates (PHA), and non-resorbable fibers, such as polyethylene terephthalate (PET) and ultra-high molecular weight polyethylene (UHMWPE). The biocompatible fibers can also be formed from mammalian collagen or plant-based collagen such as COLLAGE RH. It will be appreciated that the biocompatible fiber can be formed from other biocompatible materials, such as other biocompatible materials that are typically used in forming biocompatible fibers for in vivo medical applications.

In another example, the biocompatible polymer used to form the fibers may be radio-opaque to allow the location, integrity, and/or deformation (e.g., contraction or distension) of the tissue graft to be assessed in a living system. Such a radio-opaque fiber will also mitigate tearing of the graft, improve the fixation retention of the graft, and/or limit cyclic stretching of the graft and substantially maintain these properties following partial enzymatic degradation of the graft while one or more of its layers remodels.

Regardless of the material used for the fiber of the reinforcing means, the fiber should exhibit a high modulus of elasticity and a failure load tailored to meet particular design criterion corresponding with in vivo strength requirements of the treated tissue. For example, reinforced patches used for the treatment of large and massive rotator cuffs should exhibit failure loads of greater than about 250 Newtons (N) at a time of implantation, and greater than about 150 N after about one week of implantation in vivo. Alternatively, reinforcing patches used for the treatment of tissues experiencing lower natural loads may be required to exhibit failure loads of about 30 N to about 50 N. As another example, fiber reinforced layers used for the treatment of ventral abdominal wall defects and hernias should exhibit burst strengths greater than 50 N/cm, suture retention strengths greater than 20 N, tear resistance greater than 20 N, and strain at 16 N/cm load between about 10% and about 30%, at the time of implantation, and substantially maintain these properties after implantation in vivo until the host tissues have sufficient strength. It will be understood, however, that the fibers, their stitch design (i.e., reinforcement pattern), or the particular first and second layers can be tailored to produce failure loads of the fiber-reinforced tissue graft commensurate in scale to any tissue treated within the body.

In still other instances, at least one of the fibers, the first layer, and the second layer (where applicable) can be mechanically, chemically or biologically modified to enhance adhesion between the fibers, the first layer, and the second layer to further secure the first layer to the second layer and/or fibers to the first layer and the second layer. This modification may occur before or after attachment of the first layer to the second layer as well as before or after the fibers are incorporated into the first layer and the second layer. This modification may be performed on a portion of or substantially all of the stitched fibers or the first layer or the second layer or all three. During loading of the tissue graft, the fibers may begin to displace relative to the first layer and/or the second layer and may ultimately completely slip out from the first layer and the second layer and become the primary load bearing components of the reinforced tissue construct. It therefore becomes desirable to mitigate or prevent fiber slippage in order to ensure that usage loads are borne by the entire graft and not just the fibers. Adhesion characteristics of the fibers can be improved by ablation via ultra-violet (UV) or infrared (IR) light, UV cross-linking or chemical cross-linking, plasma etching, ion etching, coating the fibers with microspheres, application of adhesives, such as biocompatible synthetic adhesives, bioadhesives, or combinations thereof. These treatments can likewise be performed on the first layer and the second layer.

In another instance, the first layer and/or the second layer can be seeded with a single type or a plurality of differentiated cells or progenitor cells that become dispersed in the first layer and/or second layer. Examples of differentiated cells are fibroblasts, chondrocytes, osteoblasts, tenocytes, skeletal muscle cells, smooth muscle cells, endothelial cells, and neural cells. Examples of progenitor cells are bone marrow-derived progenitor cells, adipose derived stem cells, hematopoietic stem cells, endothelial progenitor cells, mesenchymal stem cells, multipotent adult progenitor cells (MAPCs), embryonic stem cells, stromal cells, and induced pluripotent stem cells. The differentiated and progenitor cells can be autologous, allogeneic, xenogeneic or a combination thereof. The differentiated and progenitor cells can also be genetically modified. Genetically modified cells can include cells that are transfected with an exogenous nucleic acid and that express a polypeptide of interest including, for example, a growth factor, a transcription factor, a cytokine, and/or a recombinant protein.

The first layer and/or second layer of the multilayer graft can additionally or optionally include at least one biologically active molecule dispersed or seeded therein. Any desired biologically active molecule can be selected for impregnating into the ECM. For example, the biologically active molecule can include antibiotics, sclerosing agents, enzymes, hormones, cytokines, colony-stimulating factors, vaccine antigens, antibodies, clotting factors, angiogenesis factors, regulatory proteins, transcription factors, receptors, structural proteins, nucleic acid therapeutic agents, such as plasmids, vectors, siRNA, and micro-RNA, and combinations thereof. The biologically active molecule can be chosen based on where the musculoskeletal graft is to be located in the subject or the physiological requirements of the subject or both. For example, if the musculoskeletal graft is used to repair a tendon, the biologically active molecule which is seeded on or into the ECM can be a growth factor such as IGF-I, TGF-$\beta$, VEGF, bFGF, BMP or combinations thereof.

Optionally, a high-molecular weight (e.g., greater than about 250 kDa) hyaluronic acid (HA) can be incorporated into the multilayer tissue graft prior to, during, or after stitching of the fibers into the first layer and/or the second layer. When incorporated into the multilayer tissue graft, HA can potentially inhibit the migration of inflammatory cells, induce the migration of non-inflammatory cells, and promote angiogenesis, which would promote integration of the tissue graft with the underlying host tissues.

The high-molecular weight HA can be cross-linked within the first layer and/or the second layer to mitigate diffusion of the HA from the first layer and/or second layer. Cross-linked, high-molecular-weight HA can be retained in the first layer and/or second layer for extended periods in vitro. An example of a cross-linked HA material that can be used in this application is prepared by substituting tyramine moieties onto the HA chains and then linking tyramines to form dityramine linkages between HA chains, effectively cross-linking or gelling the HA into the first layer and/or the second layer. Examples of dityramine-cross-linked HA composition and chemistry are disclosed in U.S. Pat. Nos. 6,982,298 and 7,465,766 and U.S. Application Publications Nos. 2004/0147673 and 2005/0265959, which are herein incorporated by reference in their entirety. The tyramine-substitution rate on the HA molecules may be about five percent based on available substitution sites as disclosed in the aforementioned publications.

TS-HA can be impregnated into the first layer and/or the second layer, and then immobilized within the first layer and/or second layer by cross-linking of the tyramine adducts to form dityramine linkages, thereby producing a cross-linked HA macromolecular network. The TS-HA can be impregnated into the first layer and/or second layer prior to or after stitching the first layer and/or second layer. The TS-HA can be used to attach fibronectin functional domains (FNfds) to the first layer and/or second layer in order to further promote healing, cell migration, and anti-inflammatory capabilities. FNfds possess the ability to bind essential growth factors that influence cell recruitment and proliferation (e.g., PDGF-BB and bFGF). The FNfds may, for example, constitute fibronectin peptide "P-12" with a C-terminal tyrosine to allow it to be cross-linked to TS-HA.

Optionally, tyramine-substituted gelatin (TS-gelatin) can be immobilized within and on the surface of fascia ECM by cross-linking of the tyramine adducts to form dityramine bridges. The TS-gelatin can elicit a host macrophage response and thus promote cellular infiltration and scaffold integration. (See for example, U.S. Pat. Nos. 6,982,298 and 8,137,688, both of which are incorporate by reference in their entirety).

Optionally, a high-molecular weight (e.g., greater than about 250 kDa) hyaluronic acid (HA) can be incorporated into the tissue graft prior to, during, or after stitching of the fibers into the ECM. When incorporated into the tissue graft, HA can potentially inhibit the migration of inflammatory cells, induce the migration of non-inflammatory cells, and promote angiogenesis, which would promote integration of the ECM with the underlying host tissues.

The high-molecular weight HA can be cross-linked within the ECM to mitigate diffusion of the HA from the ECM. Cross-linked, high-molecular-weight HA can be retained in ECM for extended periods in vitro. An example of a cross-linked HA material that can be used in this application is prepared by substituting tyramine moieties onto the HA chains and then linking tyramines to form dityramine linkages between HA chains, effectively cross-linking or gelling the HA into the ECM. Examples of dityramine-cross-linked HA composition and chemistry are disclosed in U.S. Pat. Nos. 6,982,298 and 7,465,766 and U.S. Application Publications Nos. 2004/0147673 and 2005/0265959, which are herein incorporated by reference. The tyramine-substitution rate on the HA molecules may be about five percent based on available substitution sites as disclosed in the aforementioned publications.

TS-HA can be impregnated into the ECM, and then immobilized within ECM by cross-linking of the tyramine adducts to form dityramine linkages, thereby producing a cross-linked HA macromolecular network. The TS-HA can be impregnated into the ECM prior to or after stitching the ECM. The TS-HA can be used to attach fibronectin functional domains (FNfds) to the ECM in order to further promote healing, cell migration, and anti-inflammatory capabilities. FNfds possess the ability to bind essential growth factors that influence cell recruitment and proliferation (e.g., PDGF-BB and bFGF). The FNfds may, for example, constitute fibronectin peptide "P-12" with a C-terminal tyrosine to allow it to be cross-linked to TS-HA.

One example of a multilayer tissue graft in accordance with an aspect of the application is illustrated in FIG. 1. The tissue graft 110 includes first and second layers 120 and 121 of biocompatible material. Each of the first layer 120 and the second layer 121 can include a bioremodelable collagenous material, e.g., an ECM layer, or a substantially remodelable or non-remodelable synthetic or natural material. Reinforcing means 122 are provided in the first and second layers 120 and 121 in a reinforcing pattern.

The tissue graft 110 is illustrated as having a generally rectangular strip shape (e.g., about 5 cm long by about 2 cm wide) although the graft 110 can have other shapes, such as an elliptical shape, a circular shape, a square shape, etc. (e.g., FIGS. 2-4). The graft 110 includes a top surface 124 and a substantially parallel bottom surface 126 spaced from the top surface. A first side 128 and second side 130 connect the top surface 124 to the bottom surface 126. The first and second sides 128, 130 extend generally parallel to one another. The graft 110 further includes a front surface 132 and rear surface 134 which connect the first side 128 to the second side 130. The front and rear surfaces 132, 134 extend generally parallel to one another. Each of the surfaces 124-134 is formed by the first layer 120 and the second layer 121.

The reinforcing means 122 can include at least one fiber disposed or provided within the first layer 120 and/or the second layer 121 by, for example, conventional stitching techniques. By stitching, it is meant that at least one fiber of the reinforcing means 122 is stitched into the first layer 120 and/or second layer 121 such that each stitch of the reinforcing means extends between and through both the top surface 124 and the bottom surface 126 of the first layer 120 and/or second layer 121 to securely fasten the reinforcing means to the first layer and/or second layer.

The reinforcing means 122 may exhibit any reinforcement configuration or pattern that increases the fixation properties of the graft 110. One such configuration is illustrated in FIG. 1 in which first and second fibers 140, 142 are stitched into the first layer 120 and second layer 121 in geometrically concentric configurations. Additionally or alternatively, the stitch lines of the fibers can be placed further away from the edges of the graft 110 to delay, mitigate, or prevent slipping of the fibers 140, 142 within the first layer 120 and second layer 121. Although FIG. 1 illustrates two fibers in a geometrically concentric pattern 143, it will be understood that more or fewer fibers can be stitched into the first layer 120 and second layer 121 in a geometrically concentric pattern. Additionally, it will be appreciated that additional fibers can be stitched into the first layer 120 and/or second layer 121 in other reinforcement patterns.

As shown in FIG. 1, the first fiber 140 can extend substantially parallel to, and be spaced inwardly from, the periphery of the graft 110. By way of example, the first fiber 140 can extend substantially parallel to the first and second sides 128, 130 and the front and rear surfaces 132, 134 of the graft 110 such that the first fiber exhibits a generally rectangular configuration. The first fiber 140 can comprise a plurality of interconnected stitches 141. The ends of the fiber 140 may be stitched together (not shown) to form a continuous stitching construction.

The second fiber 142 can extend substantially parallel to the first fiber 140 and be disposed radially inward of the first fiber within the graft 110. In this configuration, the first and second fibers 140, 142 form a generally geometrically concentric construction in a peripheral double pass orientation. The second fiber 142 can comprise a plurality of interconnected stitches 145. The second fiber can be substantially uniformly spaced inward from the first fiber 140 by a gap indicated by "$s_1$". The gap $s_1$ may be, for example, on the order of about 1 mm to about 3 mm (e.g., about 2 mm), although other spacing configurations will be understood. It will be appreciated that although the gap $s_1$ between the fibers 140 and 142 is substantially uniform, the gap $s_1$ may vary depending on reinforcement pattern in which the fibers 140 and 142 are stitched. The ends of the second fiber 142, like first fiber 140, may be stitched together (not shown) to form a continuous stitching construction.

The first fiber 140 and the second fiber 142 can be stitched in the graft so that the number of stitches per inch is, for example, about 10 stitches per inch to about 20 stitches per inch (e.g., about 15 stitches per inch). Generally, the more stitches per inch, the greater the strength of the reinforcing means 122 and the fixation retention properties of the tissue graft 110. In some examples, however, it may be desirable to use less stitches per inch to avoid excessive needle penetrations in the first layer 120 and/or second layer 121, which may potentially weaken the tissue graft 110.

Figure 2:
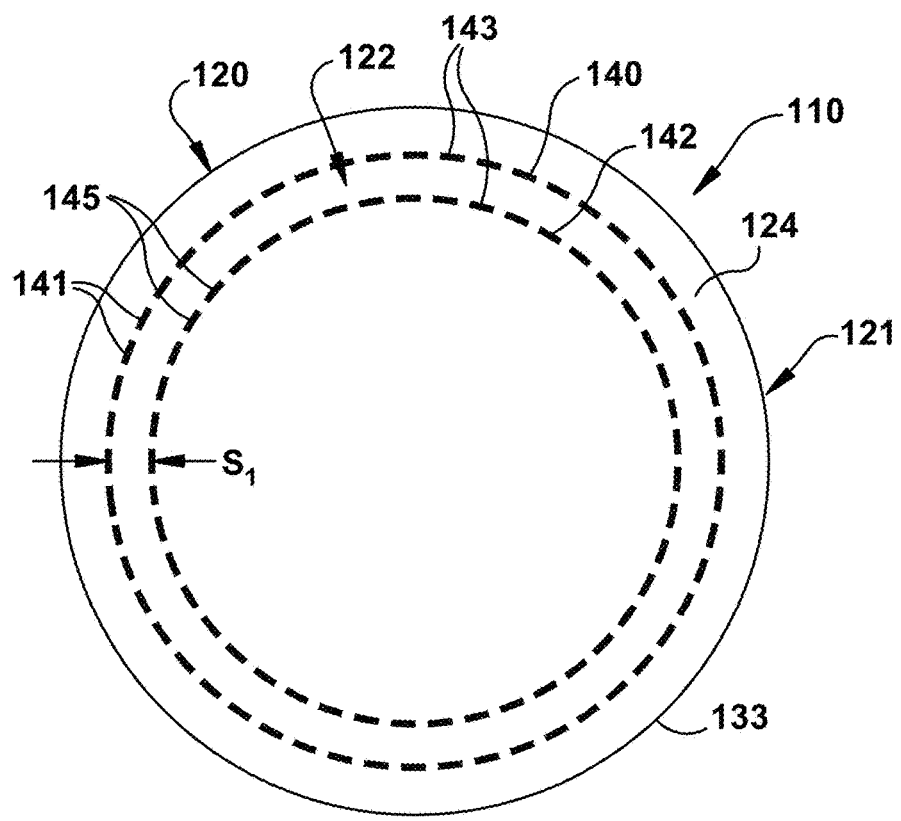
FIG. 2 is a top view of a multilayer tissue graft having a reinforcement means in accordance with another embodiment of the present invention.

Other examples of concentric reinforcement stitch patterns or configurations are illustrated in FIG. 1 and FIGS. 3A-3C. The configurations in FIG. 2 and FIGS. 3A-3C are similar to the configuration of FIG. 1, except that in FIG. 2 the graft 110 is substantially circular and therefore the reinforcing means 122 is provided in the graft in a generally circular configuration or orientation. FIG. 2 illustrates one example of a graft 110 that includes generally concentric reinforcement means 122 in a peripheral double pass orientation. The reinforcement means 122 includes a first fiber 140 that comprises a plurality of interconnected stitches 141 and a second fiber 142 that comprises a plurality of interconnected stitches 145. The first fiber 140 can extend substantially parallel to, and be spaced inwardly from, a peripheral surface 133 of the graft 110 such that the first fiber has a generally circular configuration. The second fiber 142 can extend substantially parallel to the first fiber 140 and be disposed radially inward of the first fiber within the graft 110. In this configuration, the first and second fibers 140, 142 form a generally concentric construction.

Figure 3A:
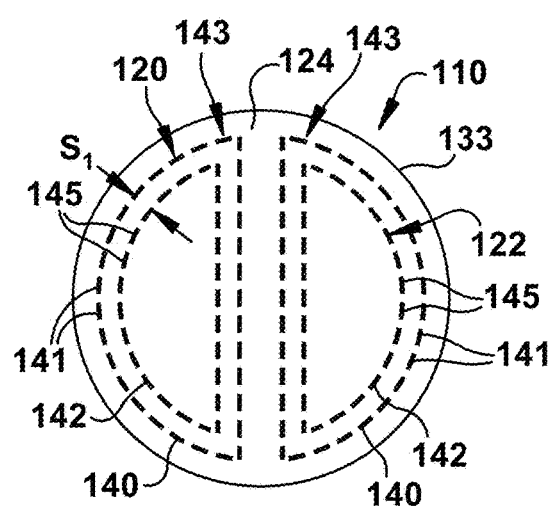
FIG. 3A is a top view of a multilayer tissue graft having a reinforcement means in accordance with yet another embodiment of the present invention.

FIG. 3A illustrates another example of the reinforcing means 122 comprising two concentric patterns 143. Each concentric pattern 143 includes a first strand 140 that comprises a plurality of interconnected stitches 141 and a second strand 142 that comprises a plurality of interconnected stitches 145. Each first fiber 140 can extend substantially parallel to, and be spaced inwardly from, a peripheral surface 133 of the graft 110 such that each first fiber has a generally circular configuration. Each second fiber 142 can extend substantially parallel to the first fiber 140 and be disposed radially inward of the first fiber within the graft 110. In this configuration, each pair of first and second fibers 140, 142 form a generally concentric construction. Although the two concentric patterns 143 are illustrated as being substantially semi-circular, it will be understood that each concentric pattern may exhibit alternative constructions such as, for example, rectangular (e.g., in a two rectangle double pass orientation), elliptical, triangular or combinations thereof within the spirit of the present invention.

Figure 3B:
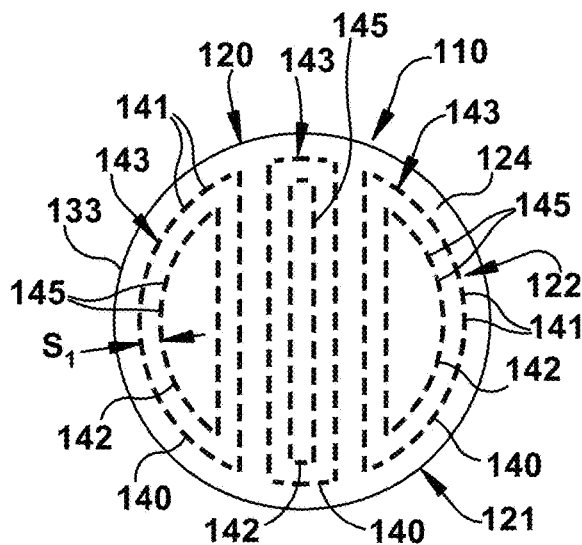
FIG. 3B is a top view of a multilayer tissue graft having a reinforcement means in accordance with yet another embodiment of the present invention.

FIG. 3B illustrates another example of the reinforcing means 122 comprising three concentric patterns 143. Each concentric pattern 143 comprises a first strand 140 comprising a plurality of interconnected stitches 141 and a second strand 142 comprising a plurality of interconnected stitches 145. Each first fiber 140 can extend substantially parallel to, and be spaced inwardly from, a peripheral surface 133 of the graft 110 such that each first fiber has a generally circular configuration. Each second fiber 142 can extend substantially parallel to the first fiber 140 and be disposed radially inward of the first fiber within the graft 110. In this configuration, each pair of first and second fibers 140, 142 form a generally concentric construction. It will be understood that each concentric pattern may exhibit any constructions such as, for example, rectangular (e.g., in a three rectangle double pass orientation), elliptical, triangular, semi-circular, circular or combinations thereof within the spirit of the present invention.

Figure 3C:
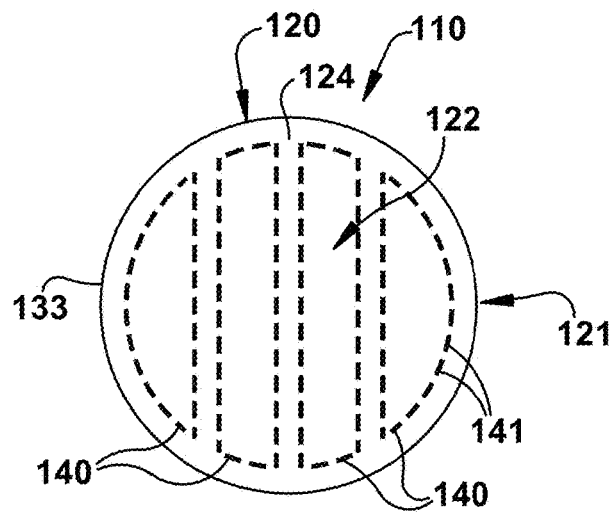
FIG. 3C is a top view of a multilayer tissue graft having a reinforcement means in accordance with yet another embodiment of the present invention.

FIG. 3C illustrates yet another example of a reinforcing means 122 that includes a plurality of first strands 140, which comprise a plurality of interconnected stitches 141 but without or free of concentric second strands 142. In particular, the first strands 140 may comprise four substantially parallel and elliptical discrete first strands. Although the four first strands 140 are illustrated as being substantially elliptical, it will be understood that each first strands may exhibit alternative constructions such as, for example, rectangular (e.g., in a four rectangle single pass orientation), semi-circular, circular, triangular or combinations thereof within the spirit of the present invention. It will also be understood that one or more of the first strands could have a geometrically concentric pattern with a second strand within the spirit of the present invention.

Figure 4A:
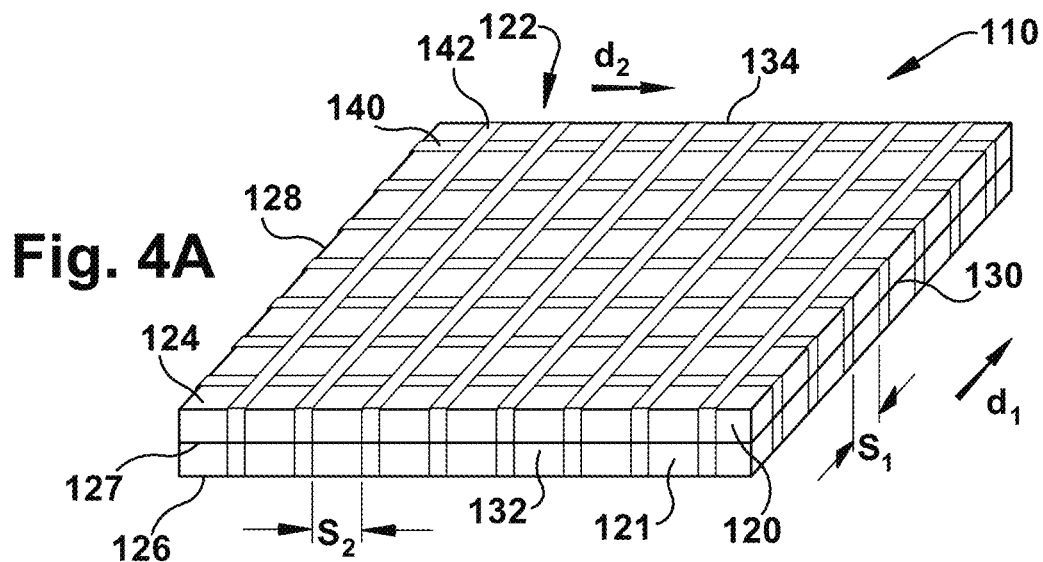
FIG. 4A is a schematic illustration of a multilayer tissue graft having a reinforcement means in accordance with yet another embodiment of the present invention.

FIG. 4A is a schematic illustration of a tissue graft 110 that includes a first layer 120, second layer 121, and a reinforcing means 122 in accordance with another example of the graft. The reinforcing means 122 includes a plurality of first fibers 140 and a plurality of second fibers 142 stitched in a cross-hatched pattern across the graft 110 and between the first and second sides 128, 130 and the front and rear surfaces 132, 134. Although FIG. 4A illustrates six first fibers 140 and eight second fibers 142, it is understood that more or less of each fiber may be utilized in accordance with the present invention. The first fibers 140 can extend in a first direction, indicated by "$d_1$", across the top surface 124 of the graft 110 from the first side 128 to the second side 130. Each of the first fibers 140 can extend parallel to one another and be spaced apart by a gap indicated by "$s_1$". The gap $s_1$ may be, for example, on the order of about 1 mm to about 3 mm, although other spacing configurations will be understood. The gap $s_1$ may be uniform or may vary between first fibers 140.

The second fibers 142 can extend in a second direction, indicated by "$d_2$", across the top surface 124 of the graft 110 from the front surface 132 to the rear surface 134. The directions "$d_1$" and "$d_2$" in which the first and second fibers 140, 142 extend may be configured such that the first fibers and the second fibers are oriented perpendicular to each other. Each of the second fibers 142 can extend parallel to one another and be spaced apart by a gap indicated by "$s_2$". The gap $s_2$ may be, for example, on the order of about 1 mm to about 3 mm, although the gap can have other spacing configurations. The gap $s_2$ may be uniform or may vary between second fibers 142. The second fibers 142 are disposed in an overlying fashion relative to the first fibers 140 such that the first fibers are disposed between the top surface 124 of the graft 110 and the second fibers. The second fibers 142, however, could alternatively be disposed between the top surface 124 of the graft 110 and the first fibers 140.

Figure 4B:
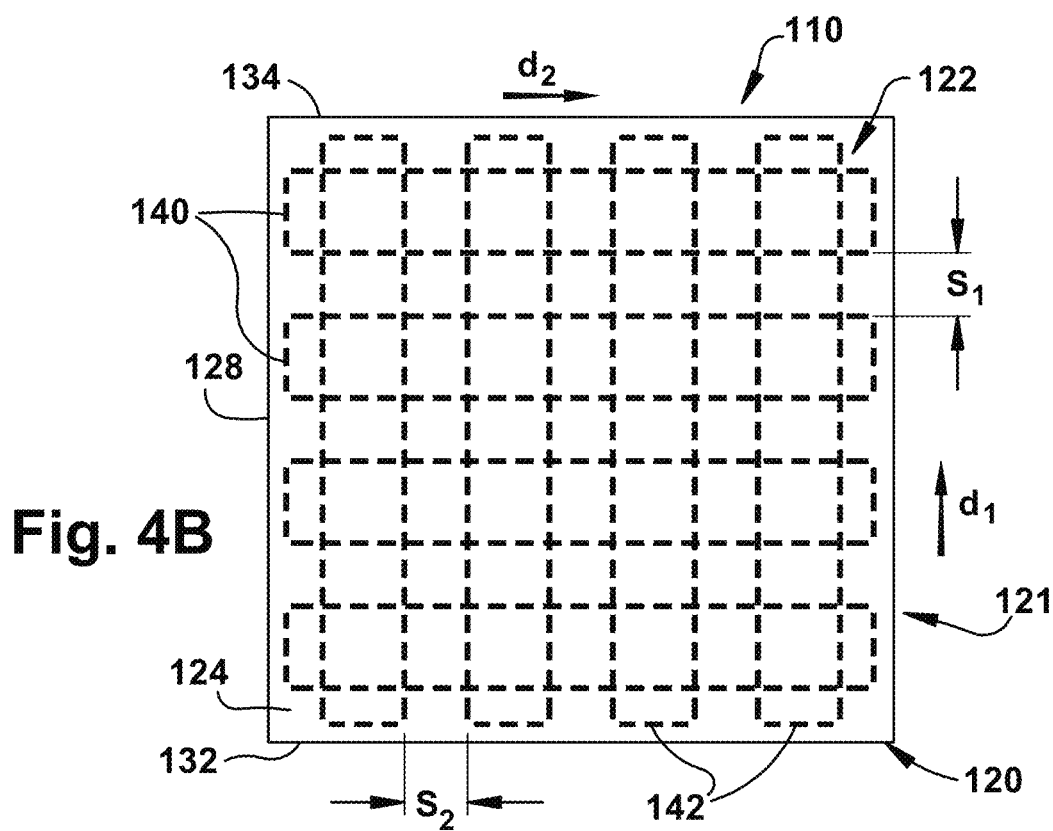
FIG. 4B is a top view of a multilayer tissue graft having a reinforcement means in accordance with yet another embodiment of the present invention.

FIG. 4B illustrates that the reinforcing means 122 comprises a plurality of first fibers 140 and a plurality of second fibers 142 stitched in a cross-hatched pattern across the graft 110 and between the first and second sides 128, 130 and the front and rear surface 132, 134. Although FIG. 4B illustrates four first fibers 140 and four second fibers 142, it is understood that more or less of each fiber may be utilized in accordance with the present invention. Each of the first fibers 140 extends from the first side 128 to the second side 130 of the graft 110. Each of the second fibers 142 extends from the front surface 132 to the rear surface 134 of the layer 120. The ends of the first fibers 140 and the ends of the second fibers 142, respectively, may be stitched together (not shown) to form a continuous stitching construction.

The second fibers 142 are disposed in an overlying fashion relative to the first fibers 140 such that the first fibers are disposed between the top surface 124 of the graft 110 and the second fibers. The second fibers 142, however, could alternatively be disposed between the top surface 124 of the graft 110 and the first fibers 140. Although the first and second fibers 140, 142 are illustrated as having a substantially rectangular shape (e.g., a rectangular cross-hatch orientation), it will be understood that the first fiber and/or the second fiber may exhibit alternative constructions such as elliptical, semi-circular, circular, triangular or combinations thereof within the spirit of the present invention.

FIGS. 5-8 illustrate various tissue graft constructions 200, 300, 400, 500 having multiple layers in accordance with another aspect of the present invention. In FIG. 5, the tissue graft 200 includes first and second layers 210, 220 of biocompatible material. Each of the first layer 210 and the second layer 220 can include a bioremodelable collagenous material (e.g., an ECM layer) or a substantially remodelable or non-remodelable synthetic or natural material. Reinforcing means 122 are provided in the first and second layers 210, 220 in a reinforcing pattern as previously described. As shown in FIG. 5, the reinforcing means 122 comprises a plurality of first fibers 140 and a plurality of second fibers 142 stitched in a cross-hatched pattern across and through both layers 210, 220 in order to mitigate tearing of the first and/or second layers, improve fixation retention of the first and/or second layers, and/or limit the cyclic stretching of the first and/or second layers and substantially maintain these properties following partial enzymatic degradation of the graft while one or more of its layers remodels.

In FIG. 6, the tissue graft 300 includes first and second layers 310, 320. The first layer 310 may constitute a bioremodelable collagenous material (e.g., an ECM layer). The second layer 320 is formed from at least two portions 322, 324 of material that are each different than the material of the first layer 310. Each portion 322, 324 of material may constitute a bioremodelable collagenous material (e.g., an ECM layer) or a substantially remodelable or non-remodelable synthetic or natural material. The portions 322, 324 of material may collectively form a second layer 320 that is the same size as the first layer 310 or a different size. The portions 322, 324 of material of the second layer 320 may abut one another or may be spaced from one another on the first layer 310. As shown in FIG. 6, the portions 322, 324 of material abut one another and are sized such that the first and second layers 310, 320 have the same size and shape. Reinforcing means 122 are provided in the first and second layers 310, 320 in a reinforcing pattern as previously described. As shown in FIG. 6, reinforcing means 122 comprises a plurality of first fibers 140 and a plurality of second fibers 142 stitched in a cross-hatched pattern across and through both layers 310, 320 in order to mitigate tearing of the first and/or second layers, improve fixation retention of the first and/or second layers, and/or limit the cyclic stretching of the first and/or second layers and substantially maintain these properties following partial enzymatic degradation of the graft while one or more of its layers remodels.

In FIG. 7, the tissue graft 400 includes first, second, and third layers 410, 420, 430. Each of the first layer 410, the second layer 420, and the third layer 430 may constitute a bioremodelable collagenous material (e.g., an ECM layer) or a substantially remodelable or non-remodelable synthetic or natural material. In one instance, the second layer 420 comprises a synthetic layer sandwiched between ECM layers 410, 430. The third layer 420 may be sized and positioned to extend across only one end of the graft 400 overlying the first layer 410 or the second layer 420. In other words, the third layer 430 only partially covers the first layer 410 or the second layer 420, thereby leaving the remainder of the first layer or the second layer exposed. Reinforcing means 122 are provided in the first, second, and third layers 410, 420, 430 in a reinforcing pattern as previously described. As shown in FIG. 7, the reinforcing means 122 comprises a plurality of first fibers 140 and a plurality of second fibers 142 stitched in a cross-hatched pattern across and through all three layers 410, 420, 430 in order to mitigate tearing of the first, second, and/or third layers, improve fixation retention of the first, second, and/or third layers, and/or limit the cyclic stretching of the first, second, and/or third layers and substantially maintain these properties following partial enzymatic degradation of the graft while one or more of its layers remodels.

In FIG. 8, the tissue graft 500 includes first, second, and third layers 510, 520, 530. Each of the first layer 510, the second layer 520, and the third layer 530 may be a bioremodelable collagenous material (e.g., an ECM layer) or a substantially remodelable or non-remodelable synthetic or natural layer. In one instance, the second layer 520 comprises a synthetic layer sandwiched between ECM layers 510, 530. Unlike the graft 400 of FIG. 7, however, the third layer 520 of the graft 500 of FIG. 8 is sized and positioned to extend across the entire first layer 510 or the second layer 520. Reinforcing means 122 are provided in the first, second, and third layers 510, 520, 530 in a reinforcing pattern as previously described. As shown in FIG. 8, the reinforcing means 122 comprises a plurality of first fibers 140 and a plurality of second fibers 142 stitched in a cross-hatched pattern across and through all three layers 510, 520, 530 in order to mitigate tearing of the first, second, and/or third layers, improve fixation retention of the first, second, and/or third layers, and/or limit the cyclic stretching of the first, second and/or third layers and substantially maintain these properties following partial enzymatic degradation of the graft while one or more of its layers remodels.

In FIGS. 5-8, the layers forming the tissue grafts 200, 300, 400 or 500 may be bonded or secured to one another prior to incorporating the reinforcing means 122 into the layers. The layers may, for example, be laminated, vacuum pressed, lyobonded (i.e., bonding using the lyophlization process), heated, partially cross-linked, etc. prior to incorporating the reinforcing means 122 into the layers. In such a case, the reinforcing means 122 not only improves fixation retention in the grafts 200, 300, 400 or 500 but also helps to minimize relative movement between layers of the grafts. Alternatively, the layers may be simply placed overlying one another prior to incorporating the reinforcing means 122 into the layers. Furthermore, some layers or portions of layers of each tissue graft 200, 300, 400 or 500 may be secured together prior to incorporating the reinforcing means 122 while other portions or layers of the tissue graft remain unsecured to other layers or portions in accordance with the present invention.

In instances where the grafts 200, 300, 400 or 500 include synthetic layers, the synthetic layers help to strengthen and reinforce the graft and facilitate the incorporation of the reinforcing means 122 into the graft. Those having ordinary skill appreciate that although grafts formed from only two and three layers are illustrated, the grafts may be formed from any number of layers of bioremodelable collagenous material or substantially remodelable or non-remodelable synthetic or natural material having reinforcing means incorporated therein in accordance with the present invention.

The tissue graft of the present invention can be used in tissue engineering and musculoskeletal repair, such as rotator cuff repair, but is not restricted to musculoskeletal applications. The graft may be administered to a subject to mechanically and biologically augment the repair. As discussed above, the tissue graft can be used as overlay (i.e., over or at the interface of the repair), an interpositional (i.e., to fill a space between a tissue and its attachment), or an underlay (i.e., under or at the interface of the repair). It will be appreciated that similar methods and materials as described herein could also be adapted to other tendon-to-bone repairs, soft-tissue repairs, such as the repair of lacerated muscles, muscle transfers, spanning a large muscle defect, or use in tendon reinforcement. These applications require secure connections between the graft 110, 200, 300, 400 or 500 and the anatomical site. Fixation techniques to soft tissue using conventional or novel suture methods, or the Pulvertaft weave technique (M. Post, J Shoulder Elbow Surg 1995; 4:1-9) may be utilized in accordance with the present invention.

Fixation techniques to bone using conventional or novel suture methods, anchors, screws, plates, adhesives, staples or tacks may be utilized in accordance with the present application. The graft 110, 200, 300, 400 or 500 may also serve as a delivery platform for the future investigation of any number of biologic strategies aimed to enhance muscular skeletal repair (e.g., rotator cuff healing). Furthermore, the graft 110, 200, 300, 400 or 500 could be effective for other needs in the field of surgical reconstruction including soft-tissue repairs, such as the repair of lacerated muscles, muscle transfers, abdominal wall reconstruction, hernia repair, repair of compartment syndrome releases, tendon reinforcement, or as a bridging material in a subject also be used as a bridging material in a subject, such as where the gap between a tendon and the associated bone is too large to repair conventionally or in abdominal wall procedures with loss of tissue domain.

The graft 110, 200, 300, 400, 500 may also serve as a platform for the future investigation of any number of graft strategies aimed to enhance muscular skeletal repair, e.g., rotator cuff healing. Furthermore, the graft 110, 200, 300, 400, 500 could be effective for other needs in the field of surgical reconstruction, including ligament reconstruction, abdominal wall repair, and tendon reconstruction in the setting of post-surgical repair failure, trauma, and segmental defects.

The following examples are illustrative of the principles and practice of this invention. Numerous additional embodiments within the scope and spirit of the invention will become apparent to those skilled in the art.

Example 1

This example shows stitching dermis and synthetic mesh together using reinforcing fiber improves the mechanical properties of the construct and mitigates tearing and/or improves fixation retention of the layers compared to using either material alone or both materials without stitching them together.

In this example, four groups were investigated:
1. Dermis (native acellular dermis)
2. Mesh (synthetic UHMWPE mesh)
3. Dermis layered against mesh (but not stitched)
4. Dermis layered against mesh and stitched together using 6PLA/2PGA polymer braids.

Uniaxial suture retention tests were used to verify the efficacy of stitching as a method to reinforce the two layers and improve the mechanical properties of the construct by mitigating tearing and/or improving fixation retention of the layers.

All human dermis grafts included allogeneic or xenogeneic dermis.

All 6PLA/2PGA braids used for reinforcing the layers were obtained from Concordia Fibers, Coventry, R.I.

Uniaxial Suture Retention Test

A sample size (n=3-4) was used in each group. Each specimen consisted of 1.5 cm wide×4.5 cm long strips of dermis and/or mesh. Dermis and mesh layers were stitched using a 6PLA/2PGA polymer braid (diameter: 400 um).

All specimens were hydrated for 30 minutes in saline solution at 37° C. A single simple suture loop of #2 Fiber-Wire was applied using a reverse cutting needle, 7.5 mm from one 1.5 cm wide edge; a template was used to assure uniformity in the placement of the sutures. The suture loop was fixed on a hook mounted on the cross head of a MTS 5543 table top system using a 100 lb load cell. The other end of the strip was clamped in 7.5 mm-deep clamps mounted on the MTS base. The specimen was stretched at 30 mm/min and the mode of failure was recorded. The suture retention load was defined as the maximum load attained by the specimen.

Figure 9:
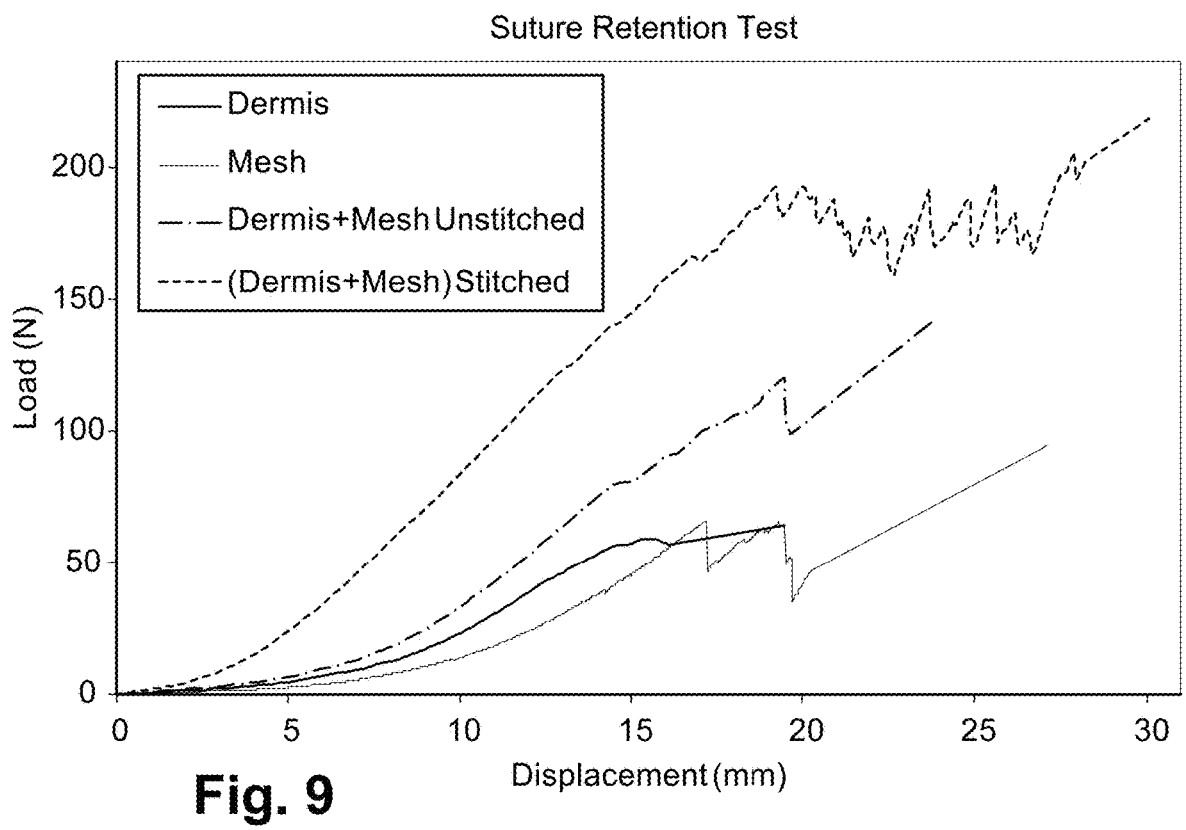
FIG. 9 is graph illustrating average load-displacement curves of dermis, synthetic mesh, dermis layered against mesh and stitched together using 6PLA/2PGA polymer braids.
Figure 10:
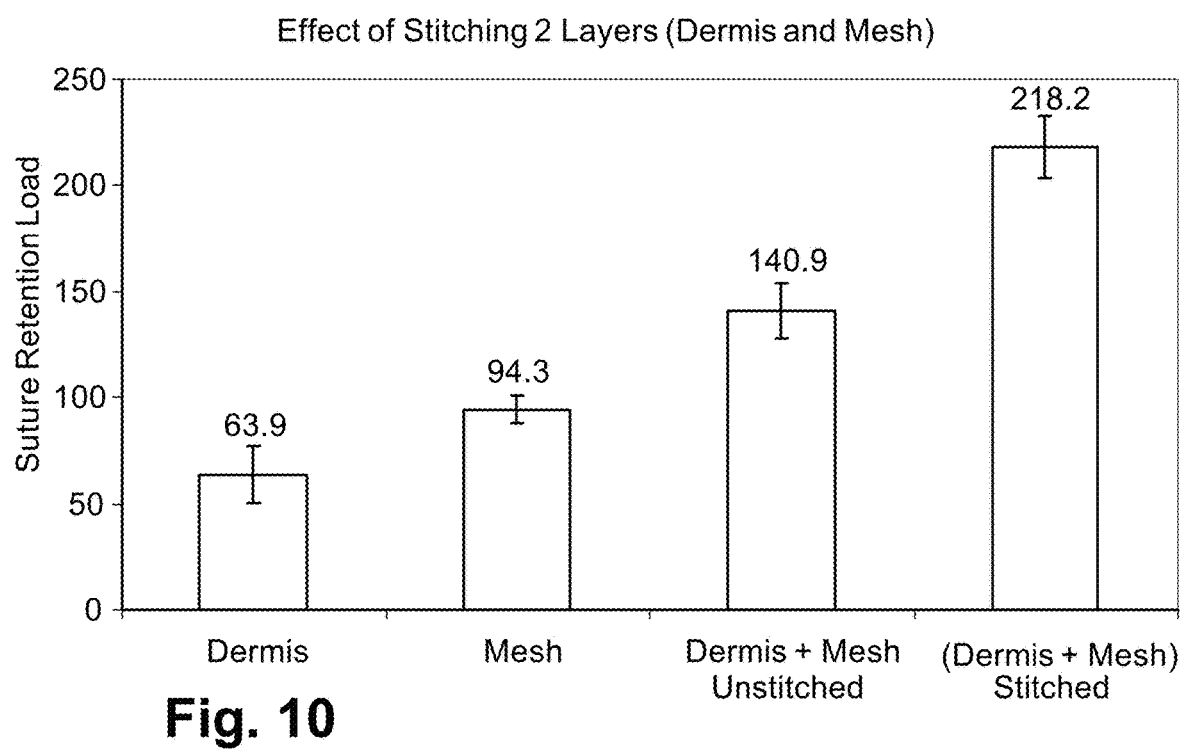
FIG. 10 is a graph illustrating increased suture retention load of dermis and mesh layers stitched together with 6PLA/2PGA polymer braids, compared to dermis or synthetic mesh alone or dermis and mesh layers unstitched.

The results of this test are illustrated in FIG. 9, FIG. 10 and Table 1. FIG. 9 (average load-displacement curves) shows that compared to the other three groups, stitching the dermis and synthetic mesh layers together increased toe-stiffness, made the load-displacement curves more linear (increased toe:linear stiffness ratio) and significantly increased suture retention load.

These data demonstrate that stitching dermis and synthetic mesh together using reinforcing fiber improves the mechanical properties of the construct and improves suture fixation retention of the layers compared to using either material alone or both materials without stitching them together.

Example 2

In this example, the biodegradable layer is stitched to a synthetic mesh layer with a stitch pattern known to impart a suture retention load to the construct that is greater than the suture retention load of the dermis alone, the mesh alone, or dermis and mesh that are not stitched together (Example 1). The biodegradable layer could be, for example, ECM derived from human allogeneic or xenogeneic dermis, the synthetic mesh could be made from polypropylene and the stitching fiber could be a PLLA/PGA braid obtained from Concordia Fibers, Coventry, R.I. In other embodiments, the synthetic mesh and the stitching fiber could be derived from other synthetic biomaterials with different biodegradation profiles (such as UHMWPE, ePTFE, PLGA and PLLA) or natural biomaterials (such as silk and collagen).

The stitched biodegradable and synthetic mesh layered constructs are hydrated for 30 minutes in saline solution at 37° C. A single simple suture loop of #2 FiberWire is applied to each construct 7.5 mm from one end using a reverse cutting needle. Samples are then incubated in 21 U/ml collagenase type I solution at 37° C. for 6 hours. Uniaxial suture retention tests are performed using a MTS 5543 table top system using a 100 lb load cell, where the suture retention load is defined as the maximum load attained by the specimen.

The suture retention properties of the stitched biodegradable and synthetic mesh layered construct are not decreased after collagenase digestion whereas the suture retention properties of the biodegradable layer with stitching but no synthetic layer are decreased modestly and the suture retention properties of the biodegradable layer alone are decreased substantially. This example demonstrates how stitching the biodegradable layer with fiber alone or in combination with a synthetic mesh can potentially substantially maintain and/or minimize the decrease in suture retention properties of the construct while the ECM is remodeling.

FIGS. 11A-15 illustrate multilayer tissue grafts 700 in accordance with yet another aspect of the present invention. The tissue grafts 700 include first and second layers 120 and 121 of biocompatible material. Each of the first layer 120 and the second layer 121 can include a bioremodelable collagenous material, e.g., an ECM layer, or a substantially remodelable or non-remodelable synthetic or natural material. Reinforcing means 122a are provided in the first and

TABLE 1

Summary of results from suture retention tests of dermis, synthetic mesh, dermis and mesh layers unstitched and dermis and mesh layers stitched together using 6PLA/2PGA polymer braids. Like letters indicate a significant difference (P < 0.05) between groups.

| | Dermis (n = 3) | Mesh (n = 4) | Dermis + Mesh Unstitched (n = 3) | (Dermis + Mesh) Stitched (n = 3) |
|---|---|---|---|---|
| Toe Stiffness (N/mm) | $0.6 \pm 0.1^{a,b}$ | $0.3 \pm 0.01^{a,c,d}$ | $0.7 \pm 0.04^{c,e}$ | $1.7 \pm 0.1^{b,d,e}$ |
| Linear Stiffness (N/mm) | $8.3 \pm 2.1^{a}$ | $9.3 \pm 1.5$ | $12.4 \pm 3.0$ | $13.7 \pm 0.1^{a}$ |
| Toe:Linear Stiffness Ratio (%) | $7 \pm 0.8^{a,b}$ | $3 \pm 0.5^{a,c,d}$ | $6 \pm 1.2^{c,e}$ | $12 \pm 1.06^{b,c,e}$ |
| Suture Retention Load (N) | $63.9 \pm 13.3^{a,b,c}$ | $94.3 \pm 6.3^{a,d,e}$ | $140.9 \pm 12.9^{b,d,f}$ | $218.2 \pm 14.3^{c,e,f}$ | second layers 120 and 121 in a reinforcing pattern. The reinforcing means 122*a* of each tissue graft 700 are similar to the reinforcing means 122 except that the reinforcing means 122*a* includes one or more free end portions that extend through and beyond the periphery of the tissue graft and are used to secure the graft to the host tissue.

The graft 700 includes a top surface 124 and a substantially parallel bottom surface 126 spaced from the top surface. A first side 128 and second side 130 connect the top surface 124 to the bottom surface 126. The first and second sides 128, 130 extend generally parallel to one another. The graft 700 further includes a front surface 132 and rear surface 134 which connect the first side 128 to the second side 130. The front and rear surfaces 132, 134 extend generally parallel to one another. Since there are multiple layers 120, 121 in each graft 700, the peripheral surfaces 128-134 of the graft include portions of both the first layer 120 and the second layer 121.

The reinforcing means 122*a* can include at least one fiber disposed or provided within the first layer 120 and/or the second layer 121 by, for example, conventional stitching techniques. By stitching, it is meant that at least one fiber of the reinforcing means 122*a* is stitched into the first layer 120 such that each stitch of the reinforcing means extends through the top surface 124 of the graft 700 and a bottom surface 127 of the first layer 120 positioned between the layers 120, 121 to securely fasten the reinforcing means to the first layer. Although the figures illustrate the reinforcing means 122*a* extending only through the first layer 120 it will be appreciated that the reinforcing means may alternatively or additionally extend through the second layer 121 of the graft 700 in any of the multilayer embodiments of FIGS. 11A-16 in accordance with the present invention.

Figure 11A:
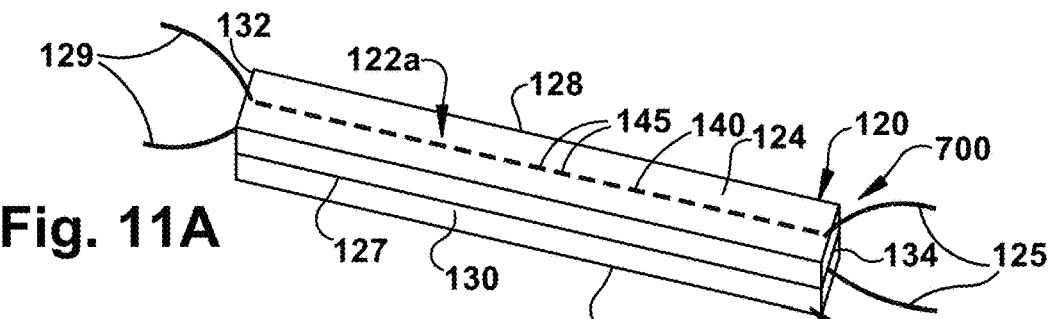
FIG. 11A is a schematic illustration of a multilayer tissue graft having a reinforcement means that extends beyond the periphery of the tissue graft in accordance with yet another aspect of the present invention.

The reinforcing means 122*a*, constituting one first fiber 140 formed from stitches 145, is integrated into the first layer 120 such that free end portions 125, 129 of the first fiber extend beyond one or more peripheral surfaces 128-134 of the graft 700. In FIG. 11A, two portions 125 of the first fiber 140 extend through the top and bottom surfaces 124, 127 and beyond the rear surface 134 of the graft 700 away from the first layer 120. Likewise, two portions 129 of the first fiber 140 extend through the top and bottom surfaces 124, 127 and beyond the front surface 132 of the graft 700 away from the first layer. As shown, one of each free end portion pair 125, 129 exits the graft 700 through the top surface 124 while the other of each free end portion pair extends between the layers 120, 121 and exits the graft adjacent the respective surface 132, 134. The portions 125, 129 thereafter extend beyond the respective surface 132, 134 and are used to secure the graft 700 to the host tissue(s) using conventional fastening techniques. It will be appreciated, however, that more or fewer (including zero) portions 125, 129 of the fiber 140 may extend beyond the respective surface 132, 134 of the graft 700 (not shown).

Figure 11B:
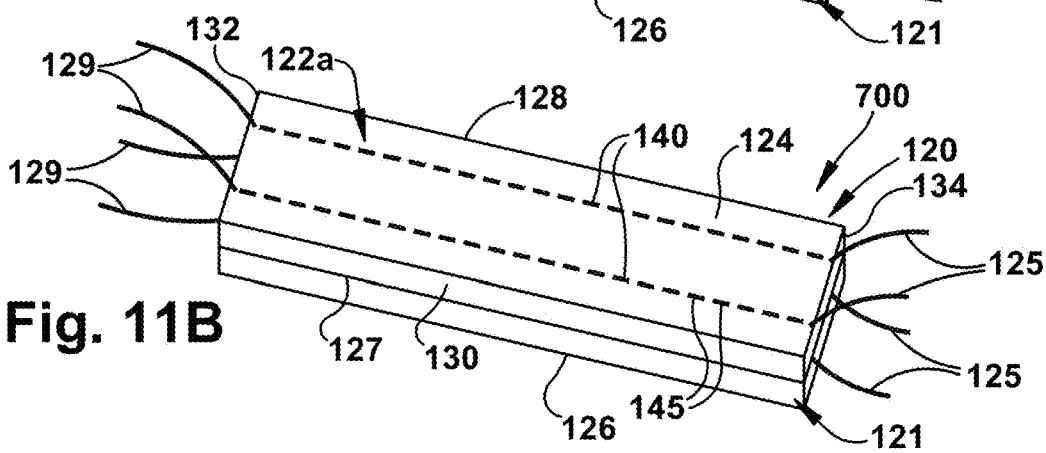
FIG. 11B is a schematic illustration of a multilayer tissue graft having a reinforcement means that extends beyond the periphery of the tissue graft in accordance with yet another aspect of the present invention.

In FIG. 11B, a pair of spaced-apart first fibers 140 extends the length of the first layer 120 and second layer 121. Each fiber 140 extends through the top surface 124 of the graft 700 and the bottom surface 127 of the first layer 120. For each fiber 140, one of each free end portion pair 125, 129 exits the graft 700 through the top surface 124 while the other of each free end portion pair extends between the layers 120, 121 and exits the graft adjacent the respective surface 132, 134. The portions 125, 129 of each first fiber 140 thereafter extend beyond the respective surfaces 132, 134. It will be appreciated, however, that more or fewer (including zero) portions 125, 129 of each fiber 140 may extend through the respective side 128, 130 of the graft 700 (not shown).

Figure 12A:
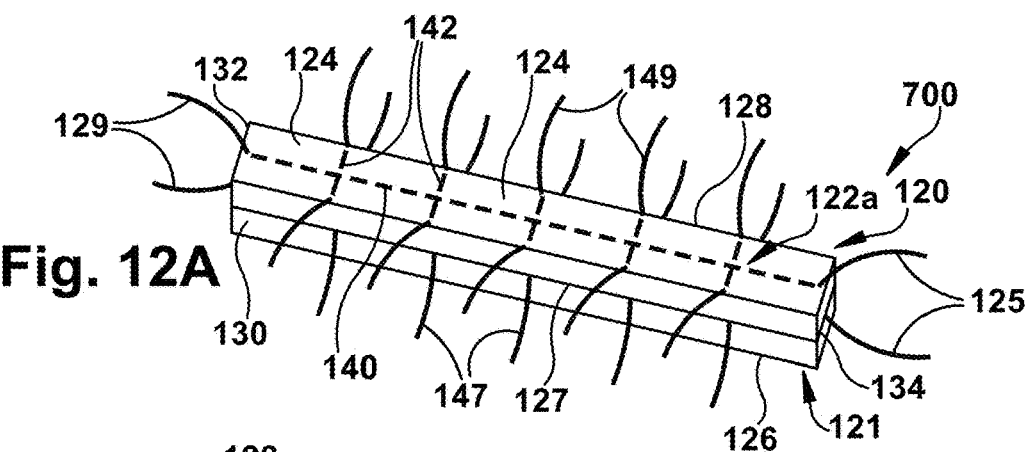
FIG. 12A is a schematic illustration of a multilayer tissue graft having a reinforcement means that extends beyond the periphery of the tissue graft in accordance with an aspect of the present invention.
Figure 12B:
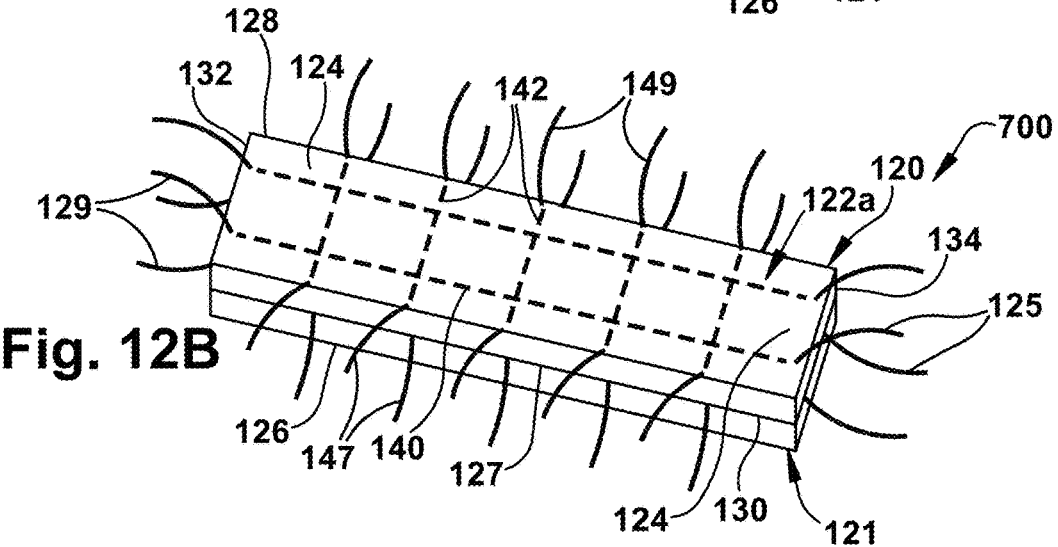
FIG. 12B is a schematic illustration of a multilayer tissue graft having a reinforcement means that extends beyond the periphery of the tissue graft in accordance with another aspect of the present invention.

Referring to FIGS. 12A and 12B, the graft 700 may further include one or more second fibers 142 that extend transverse to and intersect one first fiber 140 (FIG. 12A) or multiple first fibers 140 (FIG. 12B). The second fibers 142 may extend perpendicular to the first fiber(s) 140 or may extend at an acute or obtuse angle relative to the first fiber(s). In any case, the second fibers 142 extend through the top surface 124 of the graft 700 and the bottom surface 127 of the first layer 120. Each second fiber 142 includes one or more free end portions 147 that extend beyond the second side 130 of the graft 700 and one or more free end portions 149 that extend beyond the first side 128 of the graft. For each second fiber 142, one of each free end portion pair 125, 129 exits the graft 700 through the top surface 124 while the other of each free end portion pair extends between the layers 120, 121 and exits the graft adjacent the respective side 128, 130. It will be appreciated that more or fewer (including zero) portions 145, 147 of each second fiber 142 may extend beyond the respective side 128, 130 of the graft 700 (not shown).

Figure 13:
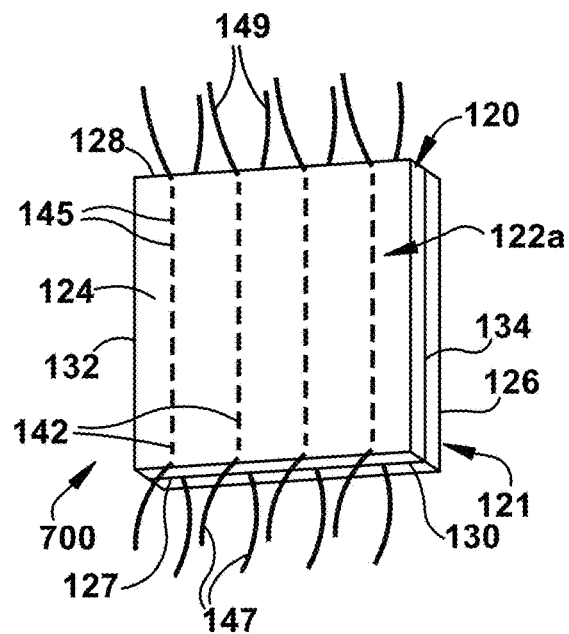
FIG. 13 is a schematic illustration of a multilayer tissue graft having a reinforcement means that extends beyond the periphery of the tissue graft in accordance with another aspect of the present invention.
Figure 14:
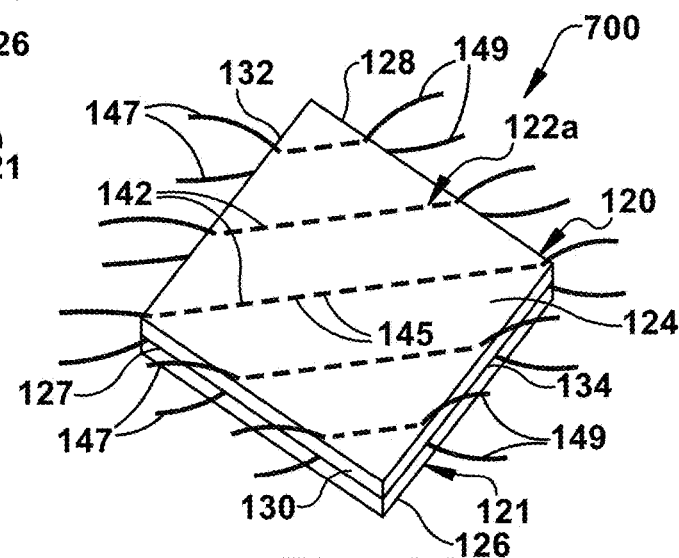
FIG. 14 is a schematic illustration of a multilayer tissue graft having a reinforcement means that extends beyond the periphery of the tissue graft in accordance with yet another aspect of the present invention.

Referring to FIGS. 13 and 14, the reinforcing means 122*a* includes a plurality of second fibers 142 while the first fiber(s) 140 are omitted. The second fibers 142 extend through the top surface 124 of the graft 700 and the bottom surface 127 of the first layer 120. Each second fiber 142 includes portions 147 that extend beyond the second side 130 and portions 149 that extend beyond the first side 128. In FIG. 14, the second strands 142 extend transversely across the tissue graft 700 such that the portions 145, 147 of each second strand extend beyond peripheral surfaces of the tissue graft that do not oppose one another, e.g., the peripheral surfaces are adjacent to one another. In other words, the portions 147, 149 of the second strands 142 do not extend solely beyond the opposing first and second sides 128, 130. Instead, the first portions 147 of the second strands 142 extend through the top and bottom surfaces 124, 127 and exit the patch 120 at both the front surface 132 and the second side 130 and extend beyond the front surface and the second side. Likewise, the second portions 149 of the second strands 142 extend through the top and bottom surfaces 124, 127 and exit the patch 120 at both the rear surface 134 and the first side 128 and extend beyond the rear surface and the first side. It will be appreciated that more or fewer (including zero) portions 147, 149 of each second fiber 142 may extend beyond the respective surfaces 130, 132 and 128, 134 of the graft 700 (not shown).

Figure 15:
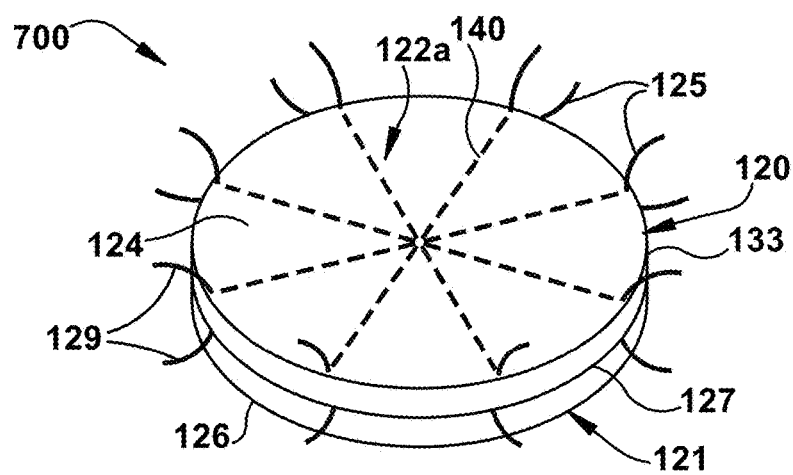
FIG. 15 is a schematic illustration of a circular multilayer tissue graft having a reinforcement means that extends beyond the periphery of the tissue graft in accordance with yet another aspect of the present invention.

Although the grafts 700 in FIGS. 11A-14 are illustrated as being rectangular or square, it will be appreciated that the graft could alternatively be, for example, circular as shown in FIG. 15. In such a case, the graft 700 has an arcuate peripheral surface 133. Each first fiber 140 extends through the top and bottom surfaces 124, 127 and beyond the peripheral surface 133 at multiple locations. The first fibers 140 may extend through or intersect at the center of the circular graft 700 or may be spaced from the center of the circular graft (not shown). Portions 125 of each first fiber 140 extend beyond one side of the surface 133 relative to the center of the graft 700 while portions 129 of each first fiber extend beyond a different side of the surface relative to the center. It will be appreciated that more or fewer (including zero) portions 125, 129 of each first fiber 140 may extend beyond different sides or portions of the surface 133 of the graft 700 (not shown).

The configuration of the reinforcement means 122*a* for the multilayer graft 700 is not limited to those shown in FIGS. 11A-15. The graft 700 may, for example, have reinforcing means 122*a* that exhibit the concentric and/or cross-hatched configurations shown in FIGS. 1-4B while including one or more free end portions that extend beyond the periphery of the tissue graft. The reinforcing means 122*a* may extend through any combination or number of layers in the multilayer configurations of FIGS. 5-8. In all instances, the reinforcement means 122a still includes at least one free end that extends beyond at least one peripheral surface of the graft 700.

Figure 16A:
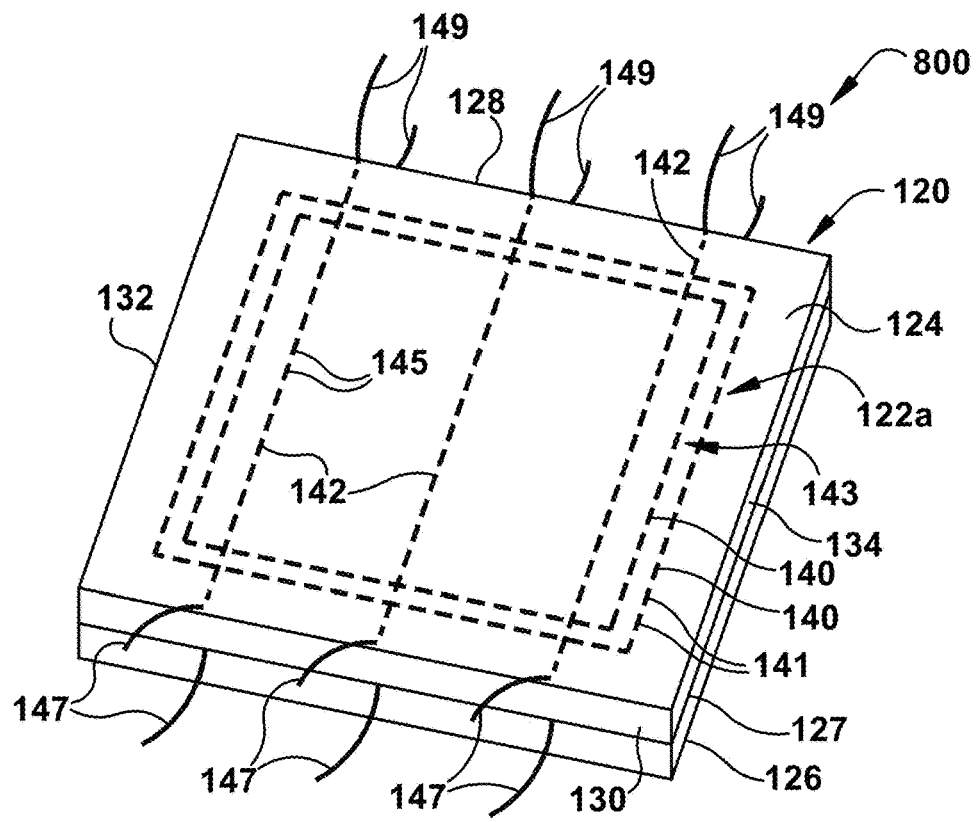
FIG. 16A is a schematic illustration of a multilayer tissue graft having reinforcement means that includes concentric and linearly extending portions with free ends that extend beyond the periphery of the tissue graft in accordance with yet another aspect of the present invention.
Figure 16B:
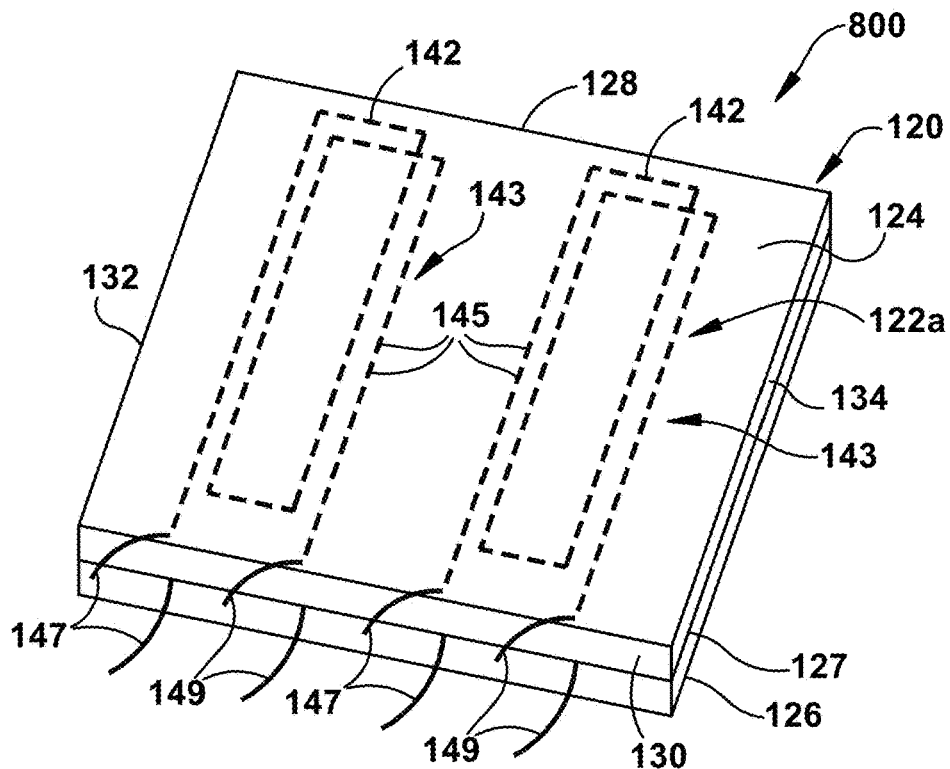
FIG. 16B is a schematic illustration of another multilayer tissue graft having reinforcement means that includes concentric and linearly extending portions with free ends that extend beyond the periphery of the tissue graft in accordance with yet another aspect of the present invention.

Another example of a tissue graft 800 in accordance with another embodiment of the present invention is illustrated in FIGS. 16A-16B. The tissue graft 800 includes an ECM patch 120 and means 122 for reinforcing the patch. In the graft 800 of FIG. 16A the reinforcing means 122 includes both a concentric pattern 143 of first fibers 140 and linearly extending second fibers 142 with one or more free end portions 147, 149 that extend through and beyond the periphery of the graft. The linearly extending second fibers 142 traverse the concentric pattern 143 of first fibers 140 although one or more of the second fibers may alternatively be spaced entirely from the concentric pattern (not shown). The portions 147, 149 of the second fibers 142 may extend through and beyond any combination of peripheral surfaces 124-134 of the graft 800.

FIG. 16B illustrates another example of reinforcing means 122 comprising two substantially concentric patterns 143 formed by a pair of second fibers 142. More specifically, each second fiber 142 forms two substantially rectangular shapes that overlap one another while both ends of the fiber extend linearly along the patch towards the second side 130. Both the portions 147 and the portions 149 of each second fiber 142 extend through the top surface 124 and bottom surface 127 and beyond the same peripheral surface 132, although the portions may extend through and beyond any combination of peripheral surfaces 124-134 of the patch 120. Although two patterns 143 are illustrated, it will be appreciated that more or fewer patterns may be provided in the patch 120 in accordance with the present invention.

The grafts 800 in FIGS. 16A-16B are illustrative and not exhaustive examples of tissue grafts that may include both concentric and linearly extending reinforcement means 122 with free ends extending through and beyond peripheral surfaces of the graft in accordance with the present invention. More specifically, tissue grafts may be provided that include the concentric patterns 143 of FIGS. 1-3B and/or the linearly extending cross-hatched pattern of FIGS. 4A-4B.

Example 3

In this example, the tissue layer is reinforced with fiber in a manner that strengthens and stiffens the tissue layer and is also used for attachment to host tissues.

Figure 17:
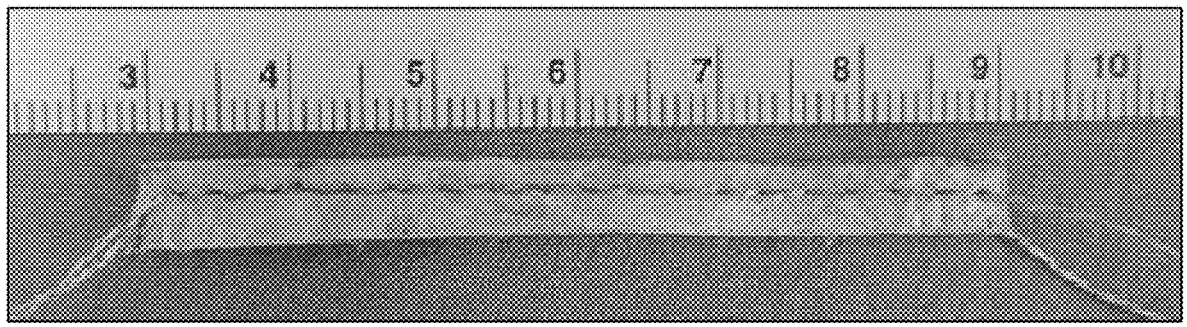
FIG. 17 is a photograph illustrating a reinforced tissue graft having a reinforcement means that extends beyond the periphery of the tissue graft.

The tissue layer could be, for example, a 0.5×6 cm strip of ECM derived from human fascia lata (Musculoskeletal Transplant Foundation, Edison, N.J.) and the fiber could be a UHMWPE braid (ForceFiber, TeleFlex Medical OEM, Kenosha, Wis.) stitched in a single pass across the tissue layer (FIG. 17).

Figure 18A:
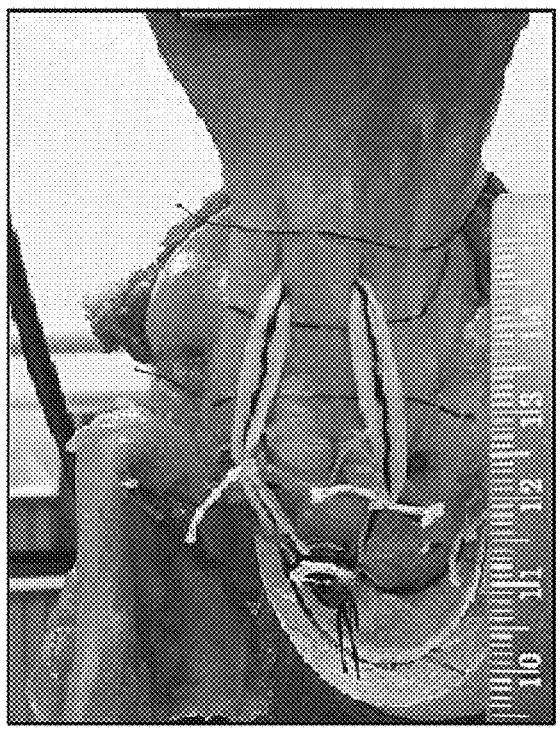
FIG. 18A is a photograph illustrating a rotator cuff repair augmented with a reinforced tissue graft having a reinforcement means that extends beyond the periphery of the tissue graft.
Figure 18B:
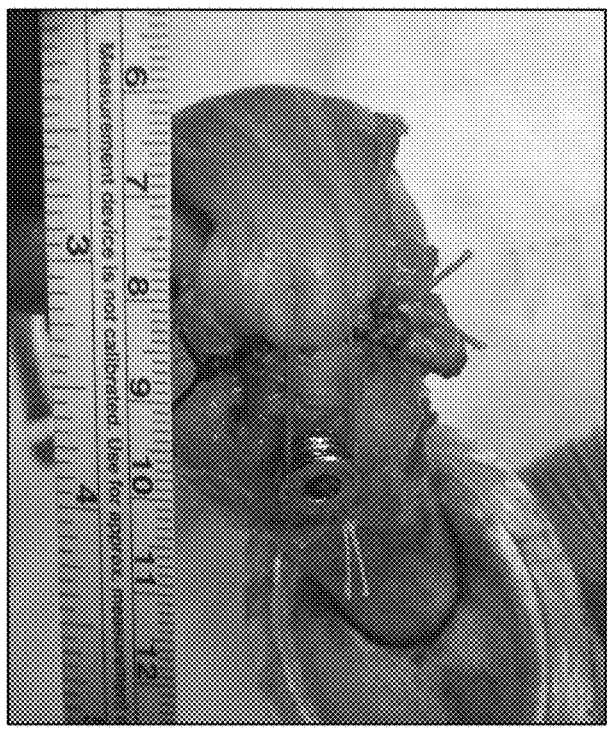
FIG. 18B is a photograph illustrating a rotator cuff repair augmented with only a reinforcing fiber.
Figure 19:
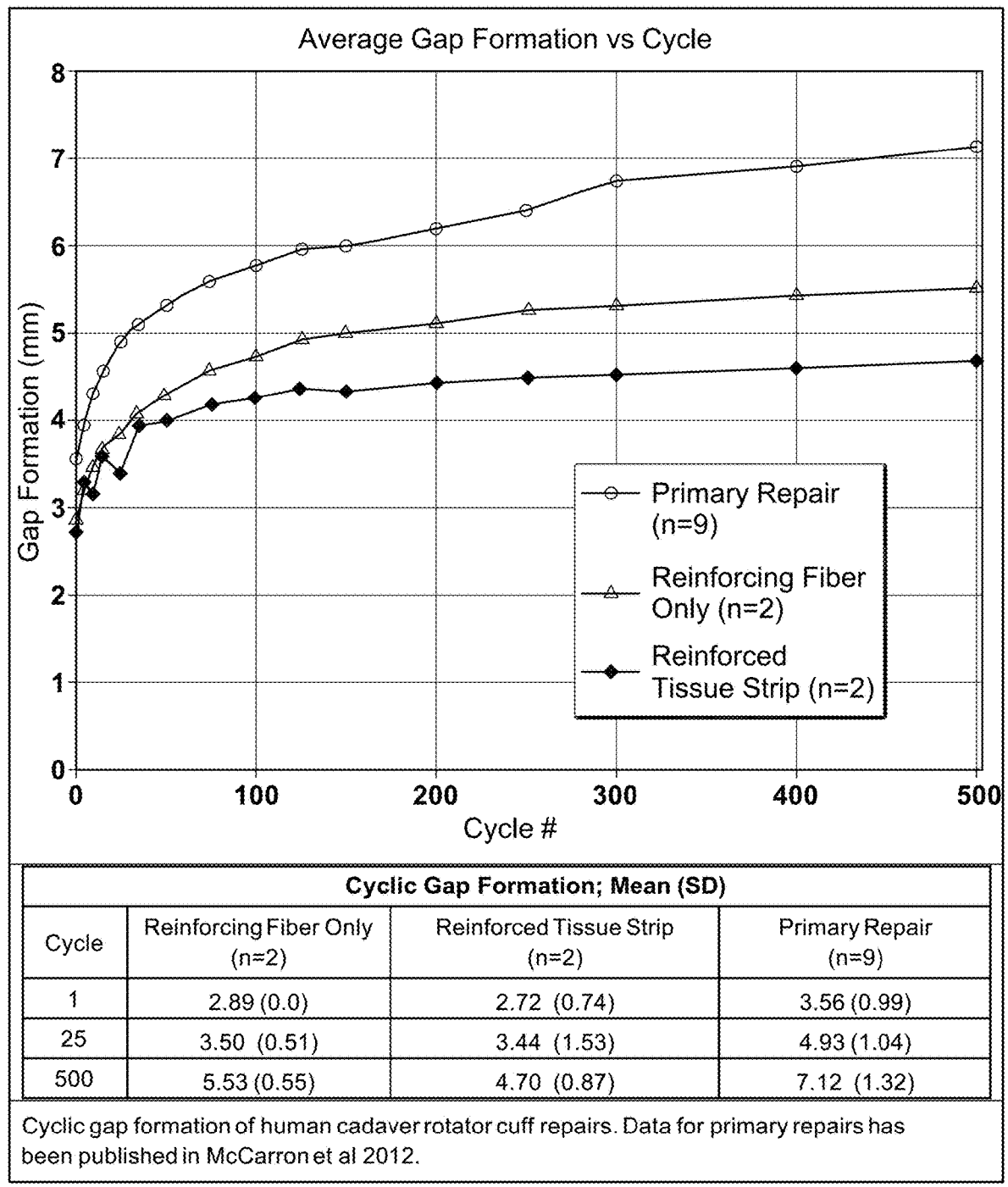
FIG. 19 is a graph illustrating the cyclic gap formation of rotator cuff repairs without augmentation or augmented with a reinforced tissue graft or a reinforcing fiber alone.

Two pairs of human cadaveric shoulders (mean age, 55±9 years) were used in this study (Anatomy Gifts Registry, Glen Burnie, Md. and ScienceCare, Aurora, Colo.). In each shoulder, the supraspinatus was sharply released from the proximal humerus and primarily repaired back to its insertion with anchors. For each pair of shoulders, one repair was randomly assigned for augmentation with a reinforced fascia strip (FIG. 18A) and the other repair was augmented with the reinforcing fiber alone (FIG. 18B). The strips or fiber alone were passed through the tendon repair approximately 1 cm medial to the repair suture line in a mattress configuration and affixed to the humerus laterally with a bone anchor. Repairs were subjected to cyclic mechanical loading of 5-180 N at 0.25 Hz for 500 cycles. Repairs were tested in air, at room temperature, and kept moist by intermittent spraying with saline solution. Optical markers were used to monitor gap formation across the repair during cyclic loading. Repair augmentation with either the reinforcing fiber alone or the reinforced tissue strip reduced cyclic gap formation compared to repairs with no augmentation (FIG. 19). Repair augmentation with the reinforced tissue strip reduced cyclic gap formation to a greater extent than augmentation with the reinforcing fiber alone (FIG. 19).

Figure 20:
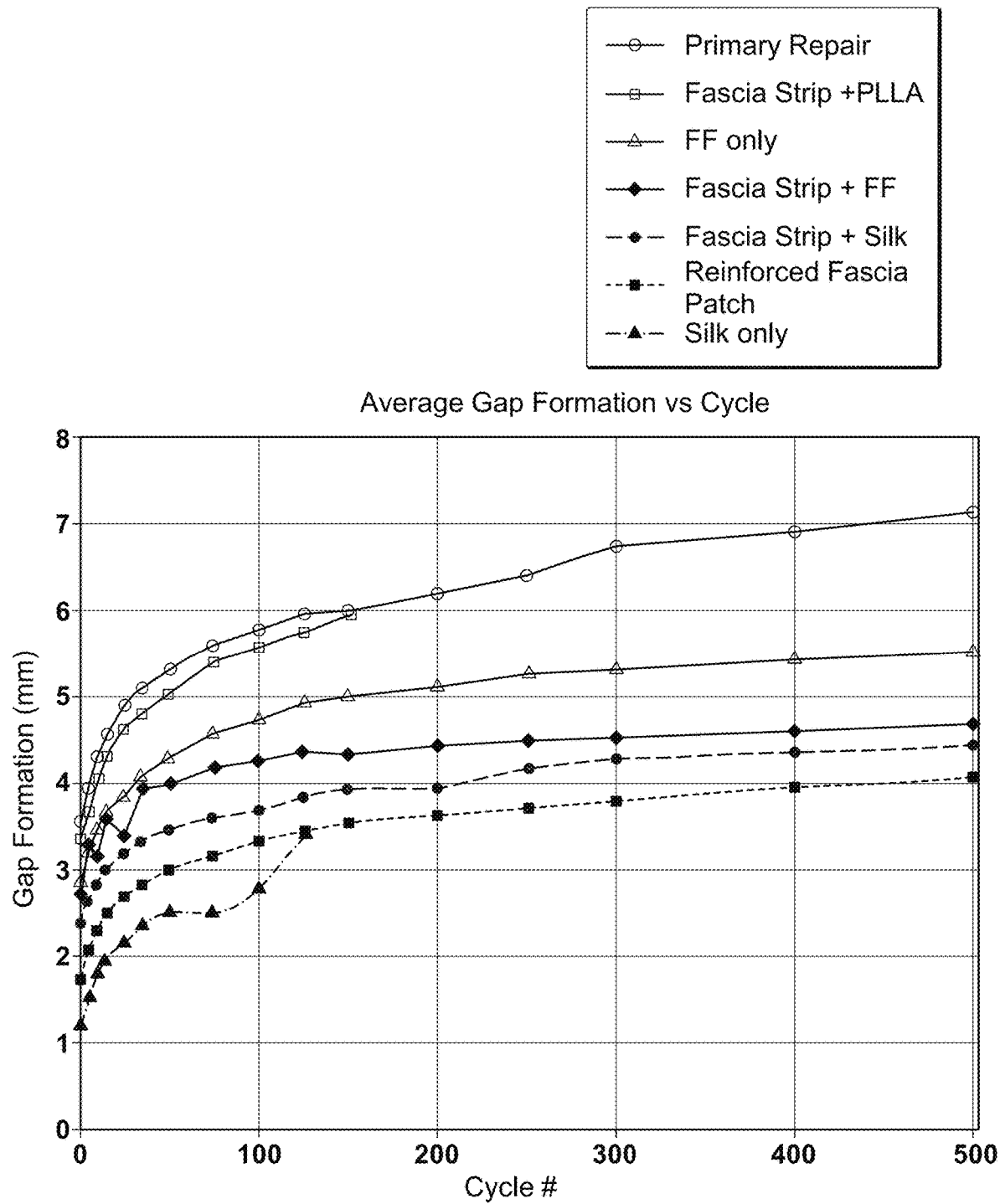
FIG. 20 is a graph illustrating the cyclic gap formation of rotator cuff repairs without augmentation or augmented with additional reinforced tissue grafts or reinforcing fibers alone.

Using a human cadaver model of rotator cuff repair, this example demonstrates how repair augmentation reduces cyclic gap formation and augmentation with a reinforced tissue strip is more mechanically advantageous than augmentation with the reinforcing fiber alone. Therefore, using the reinforced tissue strip, both the tissue and the fiber have a biomechanical role in repair augmentation. FIG. 20 compares the average gap formation for alternative configurations for both the reinforced tissue strip and the reinforcing fiber alone.

Although the results in the present example are limited to tests conducted on a single layer tissue graft, it is expected that constructing tissue grafts with multiple layers as described herein will also yield advantageous cyclic gap formation reduction results.

Example 4

In this example, the tissue layer is reinforced with fiber in a manner that limits cyclic stretching of the tissue layer following partial enzymatic degradation of the tissue. The tissue layer could include, for example, a 5×5 cm patch of ECM derived from human dermis (DermaMatrix, Musculoskeletal Transplant Foundation, Edison, N.J.) and the fiber could be a #1 PLA/PGA braid (6PLA sheath with 2PGA core, Concordia Medical, Coventry, R.I.) stitched in a cross-hatch pattern across the tissue layer. In other embodiments, the tissue layer could include an allograft material derived from other tissues, a xenograft material, a synthetic mesh or multiple layers of combinations thereof, and the stitching fiber could be derived from other synthetic biomaterials with different biodegradation profiles (such as PP, UHMWPE, ePTFE, PLGA and PLLA) or natural biomaterials (such as silk and collagen).

In this example, an in vitro accelerated enzymatic degradation model (graft degradation in collagenase solution (21 U/ml) at 37° C. for eight hours) was used to simulate in vivo degradation of an ECM graft. Native and reinforced dermis patches were mechanically tested before ("time-zero") and after enzymatic degradation (n=6/group/condition) in a custom ball-burst test setup with the patch fixed using eight peripheral mattress suture loops of #2 FiberWire to the fixture. The patches were preloaded to 10 N and then cyclically loaded 10 N-80 N (the expected physiologic load on a 5×5 cm abdominal wall patch) for 1000 cycles. The pretension elongation (PE), cyclic elongation (CE) and cumulative CE (CCE=PE+CE) were measured for each cycle. All data were analyzed by 2-way ANOVA and post hoc Tukey tests; $p<0.05$ was considered to be significant.

Figure 21:
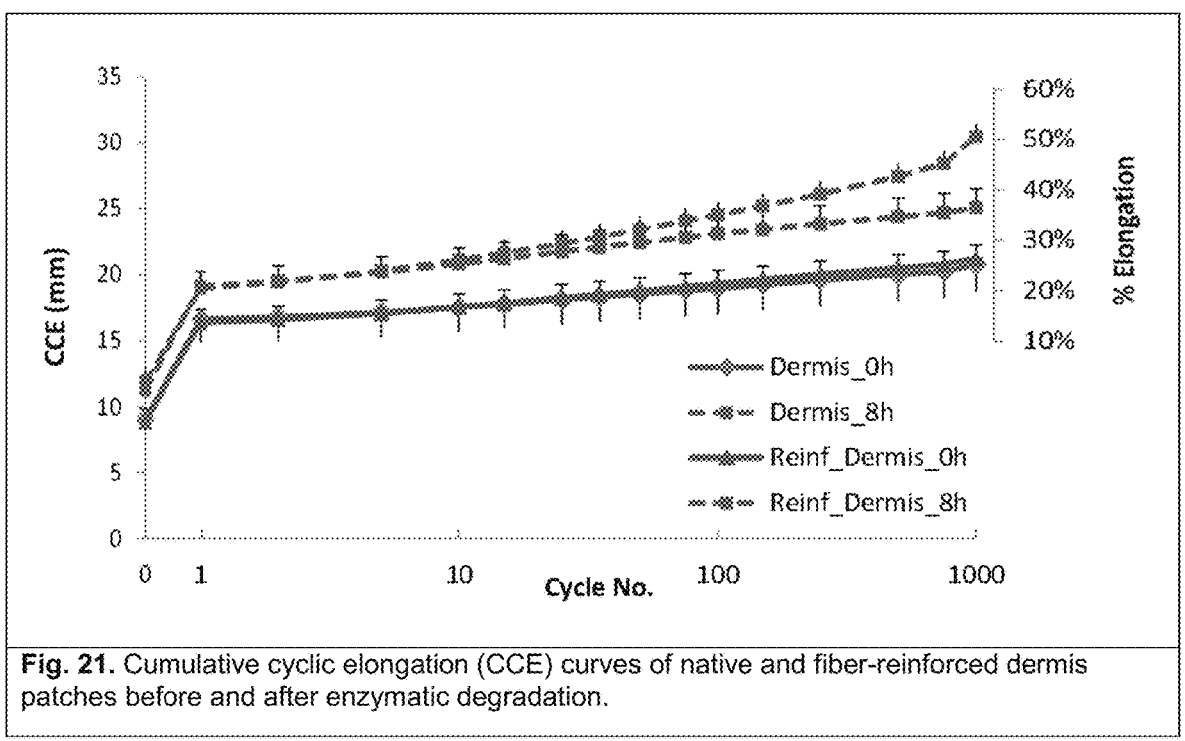
FIG. 21 is a graph illustrating cumulative cyclic elongation (CCE) curves of native and fiber-reinforced dermis patches before and after enzymatic degradation.
Figure 22:
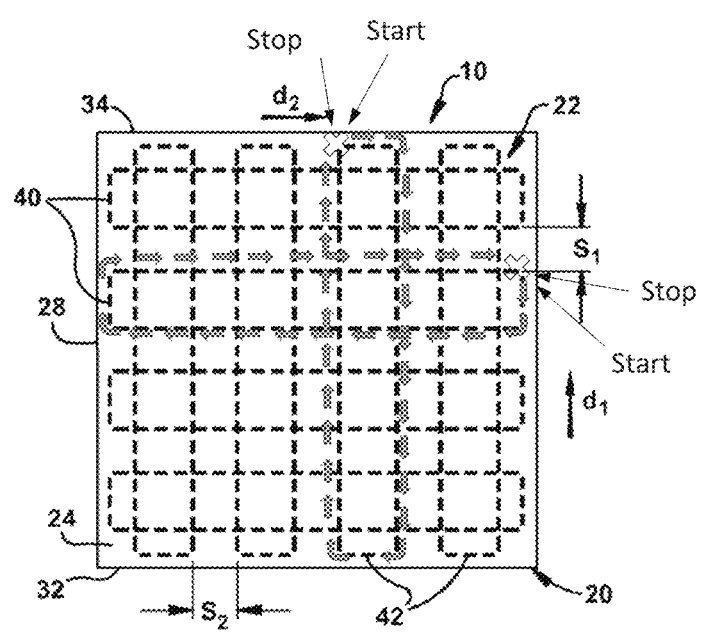
FIG. 22 is a schematic illustration of a tissue graft having a cross-hatched reinforcement means wherein the opposing terminal ends of at least one fiber of the plurality of fibers are stitched together to form a continuous stitch construction (numbers 1-16 represent the sequence in which the reinforcement means is stitched, and X represents the start/stop position where the opposing terminal ends are stitched together).

At time-zero, native and reinforced dermis patches underwent similar (~21 mm, $p=0.98$) and significant ($p<0.05$) elongation (or stretch) on cyclic loading elongation after 1000 cycles (FIG. 21 and Table 2). Enzymatic degradation resulted in significantly higher rate and amount of elongation (28.4±2.1 mm) in the native dermis group compared to the reinforced group (25.0±1.5 mm; $p<0.001$). One patch in the enzyme-degraded native dermis group failed during cyclic loading (at cycle 971).

TABLE 2

Cumulative elongation of native and fiber-reinforced dermis patches after pretensioning and cyclic loading (10-80N, 1000 cycles). Significant differences are indicated by like letters. *One patch in the enzyme-degraded native dermis group failed during cyclic loading (at cycle 971).

| Elongation (mm) | Time Zero (0h) (=6) | | Collagenase (8h) (=6) | |
| --- | --- | --- | --- | --- |
| | Native Dermis | Fiber-reinforced Dermis | Native Dermis | Fiber-reinforced Dermis |
| 10N Pretension | 9.1 ± 0.8 | 8.9 ± 1.0 | 11.9 ± 1.3 | 11.3 ± 1.1 |
| Cycle 1 | 16.6 ± 1.8 | 16.4 ± 1.0 | 19.0 ± 1.9 | 19.1 ± 1.1 |
| Cycle 10 | 17.5 ± 1.9 | 17.5 ± 1.1 | 21.1 ± 2.2 | 20.8 ± 1.2 |
| Cycle 100 | 19.0 ± 2.0 | 19.3 ± 1.2 | 24.5 ± 2.2 | 23.1 ± 1.3 |
| Cycle 1000 | 20.8 ± 2.1$^a$ | 21.2 ± 1.2$^b$ | 28.4 ± 2.1*$^{a,c}$ | 25.1 ± 1.5$^{b,c}$ |

Using an in vitro model of enzymatic degradation of ECM grafts, this example demonstrates that dermis patches reinforced with PLLA/PGA fiber limited the cyclic stretching of the grafts after partial enzymatic degradation. Therefore, the presence of reinforcing fiber is expected to limit stretching of the ECM graft after surgical implantation such as in abdominal wall and hernia repairs, and potentially improve repair outcomes by preventing repair bulging and reherniation.

Although the results in the present example are limited to tests conducted on a single layer tissue graft, it is expected that constructing tissue grafts with multiple layers as described herein will also yield advantageous, limited cyclic stretching behavior following partial enzymatic degradation of the tissue.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A biocompatible tissue graft comprising:
a first layer of a bioremodelable collagenous material comprising extracellular matrix;
a second layer of a biocompatible, non-remodelable synthetic material that is attached to the first layer; and
a plurality of fibers stitched in a cross-hatched reinforcing pattern in the first layer, or in the first layer and the second layer, to affect at least one mechanical property of the graft by mitigating tearing and/or improving fixation retention of the graft, each of the fibers comprising the plurality of fibers having opposing terminal ends;
wherein the opposing terminal ends of at least one fiber of the plurality of fibers are stitched together to form a continuous stitch construction;
wherein one or more of the mechanical properties of the graft is substantially maintained following partial enzymatic degradation of the graft while it remodels.

2. The tissue graft of claim 1, wherein the plurality of fibers comprises a natural or synthetic material.

3. The tissue graft of claim 2, wherein the first layer comprises a mammalian-derived or plant-based collagen material.

4. The tissue graft of claim 2, wherein the plurality of fibers is selected from the group consisting of collagen, silk, sericin free silk, modified silk fibroins, polyesters like PGA, PLA, polylactic-co-glycolic acid (PLGA), polyethyleneglycol (PEG), polyhydroxyalkanoates (PHA), polyethylene terephthalate (PET), polyethylene (PE), ultra-high molecular weight polyethylene (UHMWPE), blends thereof, and copolymers thereof.

5. The tissue graft of claim 1, wherein the plurality of fibers is modified to improve adhesion between the layers and the plurality of fibers.

6. The tissue graft of claim 1, wherein the extracellular matrix is decellularized.

7. The tissue graft of claim 1, wherein at least one the first layer or the second layer further comprises at least one differentiated or progenitor cell.

8. The tissue graft of claim 1, wherein at least one of the first layer or the second layer further comprises at least one biologically active molecule selected from the group consisting of drugs, sclerosing agents, enzymes, hormones, cytokines, colony-stimulating factors, vaccine antigens, antibodies, clotting factors, angiogenesis factors, regulatory proteins, transcription factors, receptors, structural proteins, nucleic acid therapeutic agents, and combinations thereof.

9. The tissue graft of claim 1, wherein at least one of the first and second fibers comprises a biocompatible material that is bioresorbable, biodegradable, or non-resorbable.

10. The tissue graft of claim 1, wherein the first layer is stitched together with the second layer such that the plurality of fibers extends between and through both a top surface of the first layer and the second layer.

* * * * *